United States Patent [19]
Knipple et al.

[11] Patent Number: 5,876,994
[45] Date of Patent: Mar. 2, 1999

[54] PHEROMONE DESATURASES

[75] Inventors: Douglas C. Knipple; Wendell L. Roelofs; Stuart J. Miller, all of Geneva, N.Y.

[73] Assignee: Cornell Research Foundation, Inc., Ithaca, N.Y.

[21] Appl. No.: 558,823

[22] Filed: Nov. 16, 1995

[51] Int. Cl.$^6$ ....................................................... C12N 9/02
[52] U.S. Cl. ................ 435/189; 435/252.3; 435/252.33; 435/320.1; 536/23.1; 536/23.2
[58] Field of Search .................................... 435/189, 134, 435/69.1, 70.1, 172.3, 252.3, 320.1, 252.33; 536/23.1, 23.2

[56] References Cited

U.S. PATENT DOCUMENTS 5,057,419 10/1991 Martin et al. ............................ 435/134
5,063,154 11/1991 Fink et al. ............................... 435/69.1

OTHER PUBLICATIONS

Wolf et al., "Properties of the Δ11–desaturase enzyme used in cabbage looper moth sex pheromone biosynthesis," *Arch. Insect Biochem. Physiol.*, 3:45–52 (1986).

Roelofs et al., "Pheromone biosynthesis in Lepidoptera," *J. Chem. Ecol.*, 14:2019–2031 (1988).

Gould et al., "Use of the DNA polymerase chain reaction for homology probing: Isolation of partial cDNA or genomic clones encoding the iron–sulfur protein of succinate dehydrogenase from several species," *Proc. Natl. Acad. Sci. USA*, 86:1934–1938 (1989).

Kamb et al., "Identification of genes from pattern formation, tyrosine kinase, and potassium channel families by DNA amplification," *Proc. Natl. Acad. Sci. USA*, 86:4372–4376 (1989).

Stukey et al., "Isolation and characterization of OLE1, a gene affecting fatty acid desaturation from *Saccharoymeces cerevisiae*," *J. Biol. Chem.*, 264:16537–16544 (1989).

Wolf et al., "Enzymes involved in the biosynthesis of sex pheromones in moths," *Reprinted from: ACS Symposium Series No. 38 389: Biocatalysis in Agricultural Biotechnology*, Whitaker et al., eds., American Chemical Society, pp. 323–332 (1989).

Zhao et al., "Sex pheromone biosynthesis in the Asian corn borer *Ostrinia furnacalis* (II): Biosynthesis of (E)–and (Z)–12–tetradecenyl acetate involves Δ14 desaturation," *Arch. Insect Biochem. Physiol.*, 15:57–65 (1990).

Stukey et al., "The OLE1 gene of *Saccharomyces cerevisiae* encodes the Δ9 fatty acid desaturase and can be functionally replaced by the rat stearoyl–CoA desaturase gene," *J. Biol. Chem.*, 265:20144–20149 (1990).

Arthington et al., "Cloning, disruption and sequence of the gene encoding yeast C–5 sterol desaturase," *Gene*, 102:39–44 (1991).

Cheneval et al., "Cell–free transcription directed by the 422 adipose P2 gene promoter: Activation by the CCAAT/enhancer binding protein," *Proc. Natl. Acad. Sci. USA*, 88:8465–8469 (1991).

Doyle et al., "PCR–based phylogenetic walking: isolation of para–homologous sodium channel gene sequences from seven insect species and an arachnid," *Insect. Biochem.*, 21:689–696 (1991).

Knipple et al., "Isolation of insect genes coding for voltage–sensitive sodium chanels and ligand–gated chloride channels by PCR–based homology probing," In Duce, I.R., ed., *Neurotox '91: Molecular Basis of Drug and Pesticide Action*, New York: Elsevier Applied Science pp. 271–283 (1991).

Knipple et al., "PCR–generated conspecific sodium channel gene probe for the house fly," *Arch. Insect Biochem. Physiol.*, 16:45–53 (1991).

Shanklin et al., "Stearoyl–acyl–carrier–protein desaturase from higher plants in structurally unrelated to the animal and fungal homologs," *Proc. Natl. Acad. Sci. USA*, 88:2510–2514 (1991).

Tang et al., "Development of functionally competent cabbage looper moth sex pheromone glands," *Insect Biochem.*, 21:573–581 (1991).

Pierce et al., "The cyanide insensitive stearoyl–CoA desaturase in the housefly, *Musca domestica*: possible interactions of cytochrome $b_5$ and cytochrome P–450," *Biochimica et Biophysica Acta*, 1125:268–273 (1992).

Rodriguez et al., "Characterization of the $\Delta^{11}$–palmitoyl–CoA–desaturase from *Spodoptera littoralis* (Lepidoptera:noctuidae," *Insect, Biochem. Molec. Biol.*, 22:143–148 (1992).

Swick et al., "Identification of a transcriptional repressor down–regulated during preadipocyte differentiation," *Proc. Natl. Acad. Sci. USA*, 89:7895–7899 (1992).

(List continued on next page.)

*Primary Examiner*—Robert A. Wax
*Assistant Examiner*—Nashaat T. Nashed
*Attorney, Agent, or Firm*—Nixon, Hargrave, Devans & Doyle LLP

[57] ABSTRACT

The present invention is directed to isolated membrane-associated acyl-CoA desaturases expressed in the pheromone gland of an insect and, in particular, the Δ11 desaturase of *Trichoplusia ni*. The present invention further relates to an isolated DNA molecule encoding the *T. ni* Δ11 desaturase, expression vectors comprising the DNA molecule, and host cells comprising the expression vectors. Methods for isolating DNA sequences of homologous acyl-CoA desaturases expressed in the pheromone glands of insects are provided. The use of these acyl-CoA desaturases, DNA molecules, expression vectors, and host cells to produce an unsaturated fatty acyl-CoA product from a saturated or unsaturated fatty acyl-CoA reactant is also disclosed. The unsaturated fatty acyl-CoA products are useful as pheromones or as pheromone precursors as well as in the preparation of organic molecules, such as drugs.

6 Claims, 14 Drawing Sheets

OTHER PUBLICATIONS

Borgeson et al., "Subcellular location of the $\Delta^{12}$ desaturase rules out bacteriocyte contribution to linoleate biosynthesis in the house cricket and the American cockroach," *Insect Biochem. Molec. Biol.*, 23:297–302 (1993).

Fox et al., "Resonance raman evidence for an Fe–O–FE center in stearoyl–ACP desaturase. Primary sequence identity with other diiron–oxo proteins," *Biochemistry*, 53:12776–12786 (1994).

Henderson et al., "PCR–based homology probing reveals a family of GABA receptor–like genes in *Drosophila melanogaster*,"*Insect Biochem. Molec. Biol.*, 24:363–371 (1994).

Shanklin et al., "Eight histidine residues are catalytically essential in a membrane–associated iron enzyme, stearoyl–CoA desaturase, and are conserved in alkane hydroxylase and xylene monooxygenase," *Biochemistry*, 33:12787–12794 (1994).

(SEQ. ID. No. 19)
(SEQ. ID. No. 20)

```
           1
RATDESAT   ................  MPAHMLQEIS  SSYTTTTTIT  EPPSGNLQNG  REK.........
OLELDESAT  MPTSGTTIEL        IDDQFPKDDS  ASSGIVDEVD  LTEANILATG  LNKKAPRIVN 51                                                              100
RATDESAT   ..............    MKKVPLYLEE  DIRPEMREDI  HDPSYQDEEG  PPPKLE.....
OLELDESAT  GFGSLMGSKE        MVSVEFDKKG  NEKKSNLDRL  LEKDNQEKEE  AKTKIHISEQ 101                                                             150
RATDESAT   ..............    YVWRNIILMA  LLHVGALYGI  TL.IPSSKVY  TLLWGIFYYL
OLELDESAT  PWTLNNWHQH        LNWLNMVLVC  GMPMIGWYFA  LSGKVPLHLN  VFLFSVFYYA 151                                                             200
RATDESAT   ISALGITAGA        HRLWSHRTYK  ARLPLRIFLI  IANTMAFQND  VYEWARDHRA
OLELDESAT  VGGVSITAGY        HRLWSHRSYS  AHWPLRLFYA  IFGCASVEGS  AKWGHSHRI 201                                                             250
RATDESAT   HHKFSETHAD        PHNSRRGFFF  SHVGWLLVRK  HPAVKEKGGK  LDMSDLKAEK
OLELDESAT  HHRYTDTLRD        PYDARRGLWY  SHMGWMLLKP  NPKYKARA..  .DITDMTDDW 251                                                             300
RATDESAT   LVMFQRRYYK        PGLLLMCFIL  PTLVPWYCWG  ETFLHSLFVS  TFLRYTLVLN
OLELDESAT  TIRFQHRHYI        LLMLLTAFVI  PTLICGYFFN  D.YMGGLIYA  GFIRVFVIQQ 301                                                             350
RATDESAT   ATWLVNSAAH        LYGYRPYDKN  IQSRENILVS  LGSVGEGFHN  YHHAFPYDYS
OLELDESAT  ATFCINSMAH        YIGTQPFDDR  RTPRDNWITA  IVTFGEGYHN  FHHEFPTDYR 351                                                             400
RATDESAT   ASEYRWH.IN        FTTFFIDCMA  ALGLAYDRKK  VSKAAV...L  ARIKRTGDGS
OLELDESAT  NA.IKWYQYD        PTKVIIYLTS  LVGLAYDLKK  FSQNAIEEAL  IQQEQKKINK

401
RATDESAT   HKSS
OLELDESAT  KKAK
```

FIG. 4

SEQ.ID.NO.9

| CAT | CGC | CTC | TGG | | | | | | | | | | | 12 |
|---|---|---|---|---|---|---|---|---|---|---|---|---|---|---|
| TCT | CAC | AAG | ACT | TTC | AAA | GCC | AAA | TTG | CCT | TTG | GAA | ATT | GTC | 64 |
| CTC | ATG | ATA | TTC | AAC | TCT | TTA | GCT | TTT | CAA | AAC | ACG | GCT | ATT | 106 |
| ACC | TGG | GCT | AGA | GAA | CAT | CGG | CTA | CAT | CAC | AAA | TAC | AGC | GAT | 148 |
| ACT | GAT | GCT | GAT | CCC | CAC | AAT | GCG | TCA | AGA | GGG | TTC | TTC | TAC | 190 |
| TCG | CAT | GTT | GGC | TGG | CTA | TTA | GTA | AAA | AAA | CAT | CCC | GAC | GTC | 232 |
| CTG | AAA | TAT | GGA | AAA | ACT | ATA | GAC | ATG | TCG | GAT | GTA | TAC | AAT | 274 |
| AAT | CCT | GTG | TTA | AAA | TTT | CAG | AAA | AAG | TAC | GCA | GTA | CCC | TTA | 316 |
| ATT | GGA | ACA | GTT | TGT | TTT | GCT | CTT | CCA | ACT | TTG | ATT | CCA | GTC | 358 |
| TAC | TGT | TGG | GGC | GAA | TCG | TGG | AAC | AAC | GCT | TGG | CAC | ATA | GCC | 400 |
| TTA | TTT | CGA | TAC | ATA | TTC | AAT | CTT | AAC | GTG | ACT | TTC | CTA | GTC | 442 |
| AAC | AGT | GCT | GCG | CAT | ATC | TGG | GGG | AAT | AAG | CCT | TAT | GAT | AAA | 484 |
| AGC | ATC | TTG | CCC | GCT | CAA | AAC | CTG | CTG | GTT | TCC | TTC | CTA | GCA | 526 |
| AGT | GGA | GAA | GGC | TTC | CAT | AAC | TTC | CAC | CAC | | | | | 556 |

FIG. 5

SEQ.ID.No.5

His Arg Leu Trp>
Ser His Lys Thr Phe Lys Ala Lys Leu Pro Leu Glu Ile Val>
Leu Met Ile Phe Asn Ser Leu Ala Phe Gln Asn Thr Ala Ile>
Thr Trp Ala Arg Glu His Arg Leu His His Lys Tyr Ser Asp>
Thr Asp Ala Asp Pro His Asn Ala Ser Arg Gly Phe Phe Tyr>
Ser His Val Gly Trp Leu Leu Val Lys Lys His Pro Asp Val>
Leu Lys Tyr Gly Lys Thr Ile Asp Met Ser Asp Val Tyr Asn>
Asn Pro Val Leu Lys Phe Gln Lys Lys Tyr Ala Val Pro Leu>
Ile Gly Thr Val Cys Phe Ala Leu Pro Thr Leu Ile Pro Val>
Tyr Cys Trp Gly Glu Ser Trp Asn Asn Ala Trp His Ile Ala>
Leu Phe Arg Tyr Ile Phe Asn Leu Asn Val Thr Phe Leu Val>
Asn Ser Ala Ala His Ile Trp Gly Asn Lys Pro Tyr Asp Lys>
Ser Ile Leu Pro Ala Gln Asn Asn Leu Leu Val Ser Phe Leu Ala>
Ser Gly Glu Gly Phe His Asn Phe His His>

FIG. 6

SEQ.ID.NO.8

| | |
|---|---|
| ATG GCT GTG ATG GCA | 15 |
| CAA ACA GTT CAA GAA ACG GCT ACA GTG TTG GAA GAG GAA GCT | 57 |
| CGC ACG ATG ACT CTA GTT GCT CCA AAG ACA ACG CCA AGG AAA | 99 |
| TAT AAA TAT ATA TAC ACC AAC TTT CTT ACA TTT TCA TAT GCG | 141 |
| CAT CTA GCT GCA TTA TAC GGA CTT TAT TTG AGC TTC ACC TCT | 183 |
| GCG AAA TGG GAA ACA TTG CTA TTC ACT TTC GTA CTC TTC CAC | 225 |
| ATG TCA AAT ATA GGC ATC ACC GCA GGG GCT CAC CGA CTC TGG | 267 |
| ACT CAC AAG ACT TTC AAA GCC AAA TTG CCT TTG GAA ATT GTC | 309 |
| CTC ATG ATA TTC AAC TCT TTA GCT TTT CAA AAC ACG GCT ATT | 351 |
| ACC TGG GCT AGA GAA CAT CGG CTA CAT CAC AAA TAC AGC GAT | 393 |
| ACT GAT GCT GAT CCC CAC AAT GCG TCA AGA GGG TTC TTC TAC | 435 |
| TCG CAT GTT GGC TGG CTA TTA GTA AAA AAA CAT CCC GAC GTC | 477 |
| CTG AAA TAT GGA AAA ACT ATA GAC ATG TCG GAT GTA TAC AAT | 519 |
| AAT CCT GTG TTA AAA TTT CAG AAA AAG TAC GCA GTA CCC TTA | 561 |
| ATT GGA ACA GTT TGT TTT GCT CTT CCA ACT TTG ATT CCA GTC | 603 |
| TAC TGT TGG GGC GAA TCG TGG AAC AAC GCT TGG CAC ATA GCC | 645 |
| TTA TTT CGA TAC ATA TTC AAT CTT AAC GTG ACT TTC CTA GTC | 687 |
| AAC AGT GCT GCG CAT ATC TGG GGG AAT AAG CCT TAT GAT AAA | 729 |
| AGC ATC TTG CCC GCT CAA AAC CTG CTG GTT TCC TTC CTA GCA | 771 |
| AGT GGA GAA GGC TTC CAT AAT TAC CAT CAC GTC TTT CCA TGG | 813 |
| GAT TAC CGC ACA GCA GAA TTA GGG AAT AAC TTC CTG AAT TTG | 855 |
| ACG ACG CTG TTC ATT GAT TTT TGT GCC TGG TTT GGA TGG GCG | 897 |
| TAT GAC TTG AAG TCT GTA TCA GAG GAT ATT ATA AAA CAG AGA | 939 |
| GCT GAA CGA ACA GGT GAC GGT TCT TCA GGG GTC ATT TGG GGA | 981 |
| TGG GAC GAC AAA GAC ATG GAC CGC GAT ATA AAA TCT AAA GCT | 1023 |
| AAC ATT TTT TAT GCT AAA AAG GAA | 1047 |

SEQ. ID. No. 4

```
Met Ala Val Met Ala>
Gln Thr Gln Glu Thr Val Ala Thr Val Leu Glu Glu Ala>
Arg Met Thr Leu Val Ala Pro Lys Thr Thr Pro Arg Lys>
Tyr Lys Tyr Ile Tyr Thr Asn Phe Leu Phe Ser Tyr Ala>
His Ala Ala Leu Tyr Gly Leu Tyr Leu Leu Ser Thr Ser>

Ala Lys Trp Glu Thr Leu Leu Phe Thr Phe Val Leu Phe His>
Met Ser Asn Ile Gly Ile Thr Ala Gly Leu Ala His Arg Leu Trp>
Thr His Lys Phe Lys Ala Lys Leu Pro Gln Leu Glu Ile Val>
Leu Met Ile Asn Ser Leu Ala Ala Phe Gln Asn Thr Ala Ile>
Thr Trp Ala Glu Arg Leu His Arg Leu Ala His Lys Tyr Ser Asp>
Thr Asp Asp Pro His Asn Ala Val His Ser Arg Gly Phe Tyr>
Ser His Val Gly Trp Leu Leu Lys Ser Arg His Pro Asp Val>
Leu Lys Tyr Gly Lys Thr Ile Met Lys Lys Asp Tyr Asn>
Asn Pro Val Leu Phe Gln Ala Leu Lys Tyr Ala Val Pro Leu>
Ile Gly Thr Cys Glu Ser Trp Asn Asn Pro Ile Ile Pro Val>
Tyr Cys Gly Gly Ile Phe Asn Asn Ala Thr Trp His Ile Ala>
Leu Phe Arg Tyr Ile His Trp Gly Leu Trp Thr Phe Leu Val>
Asn Ser Ala Ala His Gln Asn Leu Lys Pro Tyr Asp Lys>
Ser Ile Leu Pro Phe Ala Asn Leu Val Ser Ser Phe Leu Ala>
Ser Gly Gly Phe Ala Leu Tyr Gly Leu His Val Pro Trp>
Asp Tyr Arg Thr Ile Gly Cys Ala Asn Phe Leu Asn Leu>
Thr Thr Leu Phe Ser Phe Glu Ser Ile Gly Trp Ala>
Tyr Asp Lys Lys Ser Val Ser Glu Cys Tyr Lys Lys Ile Gln Arg>
Ala Glu Arg Thr Gly Asp Ser Gly Ser Ala Val Ile Trp Gly>
Trp Asp Asp Asp Met Lys Asp Asp Ser Asp Arg Ser Lys Gly>
Asn Ile Phe Tyr Ala Lys Lys Glu>
```

```
                                                                                    50
RATDESAT    ..........  ..........  MPAHMLQEIS  SSYTTTTTIT  EPPSGNLQNG  REK.......   (SEQ. ID.No.19)
T.ni        ..........  ..........  ..........  ..........  ..........  .........   (SEQ. ID.No.4)
OLELDESAT   MPTSGTTIEL  IDDQFPKDDS  ASSGIVDEVD  LTEANILATG  LNKKAPRIVN               (SEQ. ID.No.20)

100
RATDESAT    ..........  MKKVPLYLEE  DIRPEMREDI  HDPSYQDEEG  PPPKLE....
T.ni        ..........  .MAVMAQTVQ  ETATVLEEEA  RTMTLVAPKT  TPRKYK....
OLELDESAT   GFGSLMGSKE  MVSVEFDKKG  NEKKSNLDRL  LEKDNQEKEE  AKTKIHISEQ

150
RATDESAT    ..........  YVWRNIILMA  LLHVGALYGI  TL.IPSSKVY  TLLWGIFYYL
T.ni        ..........  YIYTNFLTFS  YAHLAALYGL  YLSFTSAKWE  TLLFEFVLFH
OLELDESAT   PWTLNNWHQH  LNWLNMVLVC  GMPMIGWYFA  LSGKVPLHLN  VFLFSVFYYA

200
RATDESAT    ISALGITAGA  HRLWSHRTYK  ARLPLRIFLI  IANTMAFQND  VYEWARDHRA
T.ni        MSNIGITAGA  HRLWTHKTFK  AKLPLEIVLM  IFNSLAFQNT  AITWAREHRL
OLELDESAT   VGGVSITAGY  HRLWSHRSYS  AHWPLRLFYA  IFGCASVEGS  AKWGHSHRI

250
RATDESAT    HHKFSETHAD  PHNSRRGFFF  SHVGWLLVRK  HPAVKEKGGK  LDMSDLKAEK
T.ni        HHKYSDTDAD  PHNASRGFFY  SHVGWLLVKK  HPDVLKYGKT  IDMSDVYNNP
OLELDESAT   HHRYTDTLRD  PYDARRGLWY  SHMGWMLLKP  NPKYKARA..  .DITDMTDDW

300
RATDESAT    LVMFQRRYYK  PGLLLMCFIL  PTLVPWYCWG  ETFLHSLFVS  TFLRYTLVLN
T.ni        VLKFQKKYAV  PLIGTVCFAL  PTLIPVYCWG  ESWNNAWHI.  ALFRYIFNLN
OLELDESAT   TIRFQHRHYI  LLMLLTAFVI  PTLICGYFFN  D.YMGGLIYA  GFIRVFVIQQ
```

FIG. 9A

```
        301
RATDESAT     ATWLVNSAAH LYGYRPYDKN IQSRENILVS LGSVGEGFHN YHHAFPYDYS
T.ni         VTFLVNSAAH IWGNKPYDKS ILPAQNLLVS FLASGEGFHN YHHVFPWDYR
OLELDESAT    ATFCINSMAH YIGTQPFDDR RTPRDNWITA IVTFGEGYHN FHHEFPTDYR 351                                                     400
RATDESAT     ASEYRWH.IN FTTFFIDCMA ALGLAYDRKK VSKAAV...L ARIKRTGDGS
T.ni         TAELGNNFLN LTTLFIDFCA WFGWAYDLKS VSEDII...K QRAERTGDGS
OLELDESAT    NA.IKWYQYD PTKVIIYLTS LVGLAYDLKK FSQNAIEEAL IQQEQKKINK 401                                                     450
RATDESAT     HKSS*      .......... .......... .......... ..........
T.ni         SGVIWGWDDK DMDRDIKSKA NIFYAKKE.. .......... ..........
OLELDESAT    KKAKINWGPV LTDLPMWDKQ TFLAKSKENK GLVIISGIVH DVSGYISEHP 451                                                     500
RATDESAT     .......... .......... .......... .......... ..........
T.ni         .......... .......... .......... .......... ..........
OLELDESAT    GGETLIKTAL GKDATKAFSG GVYRHSNAAQ NVLADMRVAV IKESKNSAIR 501        516
RATDESAT     .......... ......
T.ni         .......... ......
OLELDESAT    MASKRGEIYE TGKFF*
```

FIG. 9B

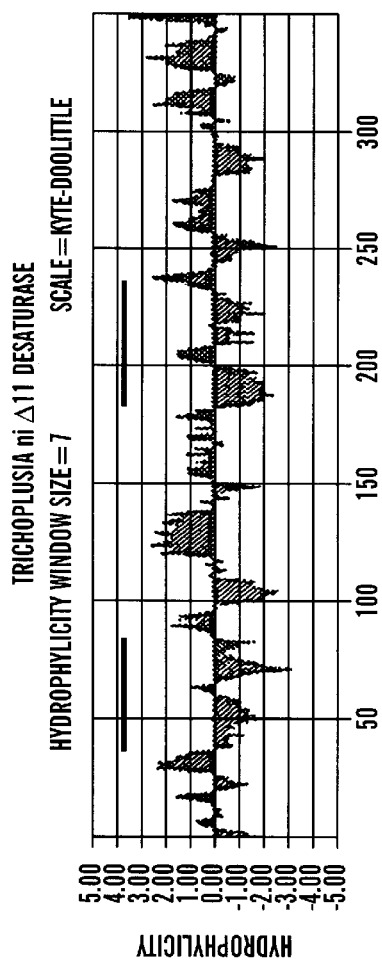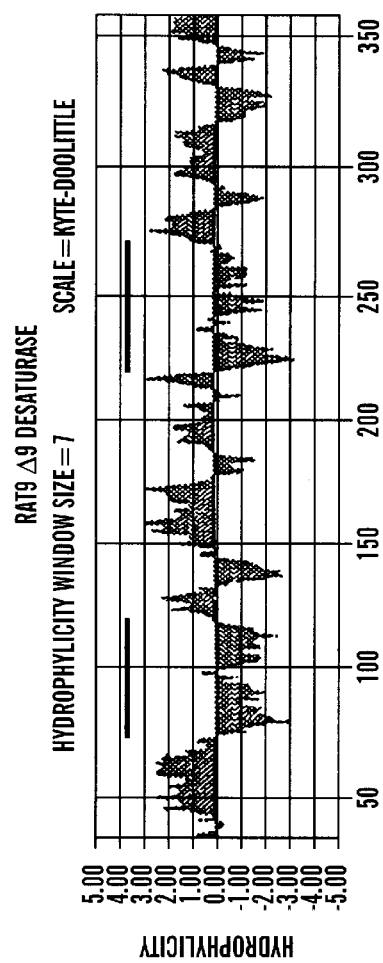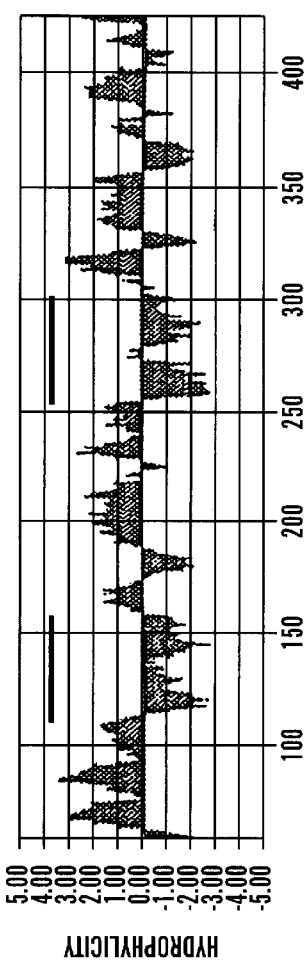
FIG. 10A
FIG. 10B
FIG. 10C

5,876,994

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:1:

His   Xaa   Xaa   Xaa   Xaa   His
    1                               5

( 2 ) INFORMATION FOR SEQ ID NO:2:

( i ) SEQUENCE CHARACTERISTICS:
    ( A ) LENGTH: 5 amino acids
    ( B ) TYPE: amino acid
    ( C ) STRANDEDNESS:
    ( D ) TOPOLOGY: linear ( i i ) MOLECULE TYPE: protein ( x i ) SEQUENCE DESCRIPTION: SEQ ID NO:2:

His Xaa Xaa His His
1               5

( 2 ) INFORMATION FOR SEQ ID NO:3:

( i ) SEQUENCE CHARACTERISTICS:
    ( A ) LENGTH: 181 amino acids
    ( B ) TYPE: amino acid
    ( C ) STRANDEDNESS:
    ( D ) TOPOLOGY: linear ( i i ) MOLECULE TYPE: protein ( x i ) SEQUENCE DESCRIPTION: SEQ ID NO:3:

His Xaa Xaa Xaa Xaa His Xaa Xaa Xaa Xaa Xaa Xaa Xaa Xaa Xaa
1               5               10                              15

Xaa Xaa Xaa Xaa Xaa Xaa Xaa Xaa Xaa Xaa Xaa Xaa Xaa Xaa Xaa
            20                          25                          30

Xaa Xaa Xaa Xaa His Xaa Xaa His His Xaa Xaa Xaa Xaa Xaa Xaa
            35                          40                          45

Xaa Xaa Xaa Xaa Xaa Xaa Xaa Xaa Xaa Xaa Xaa Xaa Xaa Xaa Xaa
    50                              55                          60

Xaa Xaa Xaa Xaa Xaa Xaa Xaa Xaa Xaa Xaa Xaa Xaa Xaa Xaa Xaa
65                              70                          75                          80

Xaa Xaa Xaa Xaa Xaa Xaa Xaa Xaa Xaa Xaa Xaa Xaa Xaa Xaa Xaa
                85                              90                          95

Xaa Xaa Xaa Xaa Xaa Xaa Xaa Xaa Xaa Xaa Xaa Xaa Xaa Xaa Xaa
            100                         105                         110

Xaa Xaa Xaa Xaa Xaa Xaa Xaa Xaa Xaa Xaa Xaa Xaa Xaa Xaa Xaa
        115                         120                         125

Xaa Xaa Xaa Xaa Xaa Xaa Xaa Xaa Xaa Xaa Xaa Xaa Xaa Xaa Xaa
    130                         135                         140

Xaa Xaa Xaa Xaa Xaa Xaa Xaa Xaa Xaa Xaa Xaa Xaa Xaa Xaa Xaa
145                         150                         155                         160

Xaa Xaa Xaa Xaa Xaa Xaa Xaa Xaa Xaa Xaa Xaa Xaa Xaa Xaa Xaa
                165                         170                         175

His Xaa Xaa His His
            180

( 2 ) INFORMATION FOR SEQ ID NO:4:

( i ) SEQUENCE CHARACTERISTICS:
    ( A ) LENGTH: 349 amino acids
    ( B ) TYPE: amino acid
    ( C ) STRANDEDNESS:
    ( D ) TOPOLOGY: linear ( i i ) MOLECULE TYPE: protein ( x i ) SEQUENCE DESCRIPTION: SEQ ID NO:4:

Met Ala Val Met Ala Gln Thr Val Gln Glu Thr Ala Thr Val Leu Glu
1               5               10                              15

Glu Glu Ala Arg Thr Met Thr Leu Val Ala Pro Lys Thr Thr Pro Arg

|  |  |  | 20 |  |  |  |  | 25 |  |  |  |  | 30 |  |  |
|---|---|---|---|---|---|---|---|---|---|---|---|---|---|---|---|
| Lys | Tyr | Lys<br>35 | Tyr | Ile | Tyr | Thr | Asn<br>40 | Phe | Leu | Thr | Phe | Ser<br>45 | Tyr | Ala | His |
| Leu | Ala | Ala<br>50 | Leu | Tyr | Gly | Leu<br>55 | Tyr | Leu | Ser | Phe | Thr<br>60 | Ser | Ala | Lys | Trp |
| Glu<br>65 | Thr | Leu | Leu | Phe | Thr<br>70 | Phe | Val | Leu | Phe | His<br>75 | Met | Ser | Asn | Ile | Gly<br>80 |
| Ile | Thr | Ala | Gly | Ala<br>85 | His | Arg | Leu | Trp | Thr<br>90 | His | Lys | Thr | Phe | Lys<br>95 | Ala |
| Lys | Leu | Pro | Leu<br>100 | Glu | Ile | Val | Leu | Met<br>105 | Ile | Phe | Asn | Ser | Leu<br>110 | Ala | Phe |
| Gln | Asn | Thr<br>115 | Ala | Ile | Thr | Trp | Ala<br>120 | Arg | Glu | His | Arg | Leu<br>125 | His | His | Lys |
| Tyr | Ser | Asp<br>130 | Thr | Asp | Ala | Asp<br>135 | Pro | His | Asn | Ala | Ser<br>140 | Arg | Gly | Phe | Phe |
| Tyr<br>145 | Ser | His | Val | Gly | Trp<br>150 | Leu | Leu | Val | Lys | Lys<br>155 | His | Pro | Asp | Val | Leu<br>160 |
| Lys | Tyr | Gly | Lys | Thr<br>165 | Ile | Asp | Met | Ser | Asp<br>170 | Val | Tyr | Asn | Asn | Pro<br>175 | Val |
| Leu | Lys | Phe | Gln<br>180 | Lys | Lys | Tyr | Ala | Val<br>185 | Pro | Leu | Ile | Gly | Thr<br>190 | Val | Cys |
| Phe | Ala | Leu<br>195 | Pro | Thr | Leu | Ile | Pro<br>200 | Val | Tyr | Cys | Trp | Gly<br>205 | Glu | Ser | Trp |
| Asn | Asn<br>210 | Ala | Trp | His | Ile | Ala<br>215 | Leu | Phe | Arg | Tyr | Ile<br>220 | Phe | Asn | Leu | Asn |
| Val<br>225 | Thr | Phe | Leu | Val | Asn<br>230 | Ser | Ala | Ala | His | Ile<br>235 | Trp | Gly | Asn | Lys | Pro<br>240 |
| Tyr | Asp | Lys | Ser | Ile<br>245 | Leu | Pro | Ala | Gln | Asn<br>250 | Leu | Leu | Val | Ser | Phe<br>255 | Leu |
| Ala | Ser | Gly | Glu<br>260 | Gly | Phe | His | Asn | Tyr<br>265 | His | His | Val | Phe | Pro<br>270 | Trp | Asp |
| Tyr | Arg | Thr<br>275 | Ala | Glu | Leu | Gly | Asn<br>280 | Asn | Phe | Leu | Asn | Leu<br>285 | Thr | Thr | Leu |
| Phe | Ile<br>290 | Asp | Phe | Cys | Ala | Trp<br>295 | Phe | Gly | Trp | Ala | Tyr<br>300 | Asp | Leu | Lys | Ser |
| Val<br>305 | Ser | Glu | Asp | Ile | Ile<br>310 | Lys | Gln | Arg | Ala | Glu<br>315 | Arg | Thr | Gly | Asp | Gly<br>320 |
| Ser | Ser | Gly | Val | Ile<br>325 | Trp | Gly | Trp | Asp | Asp<br>330 | Lys | Asp | Met | Asp | Arg<br>335 | Asp |
| Ile | Lys | Ser | Lys<br>340 | Ala | Asn | Ile | Phe | Tyr<br>345 | Ala | Lys | Lys | Glu |  |  |  |

( 2 ) INFORMATION FOR SEQ ID NO:5:

( i ) SEQUENCE CHARACTERISTICS:
        ( A ) LENGTH: 182 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:5:

| His<br>1 | Arg | Leu | Trp | Ser<br>5 | His | Lys | Thr | Phe | Lys<br>10 | Ala | Lys | Leu | Pro | Leu<br>15 | Glu |
|---|---|---|---|---|---|---|---|---|---|---|---|---|---|---|---|
| Ile | Val | Leu | Met<br>20 | Ile | Phe | Asn | Ser | Leu<br>25 | Ala | Phe | Gln | Asn | Thr<br>30 | Ala | Ile |

|     |     |     |     |     |     |     |     |     |     |     |     |     |     |     |
|---|---|---|---|---|---|---|---|---|---|---|---|---|---|---|
| Thr | Trp | Ala | Arg | Glu | His | Arg | Leu | His | His | Lys | Tyr | Ser | Asp | Thr | Asp |
|     |     | 35  |     |     |     |     | 40  |     |     |     |     | 45  |     |     |
| Ala | Asp | Pro | His | Asn | Ala | Ser | Arg | Gly | Phe | Phe | Tyr | Ser | His | Val | Gly |
|     | 50  |     |     |     |     | 55  |     |     |     |     | 60  |     |     |     |     |
| Trp | Leu | Leu | Val | Lys | Lys | His | Pro | Asp | Val | Leu | Lys | Tyr | Gly | Lys | Thr |
| 65  |     |     |     |     | 70  |     |     |     |     | 75  |     |     |     |     | 80  |
| Ile | Asp | Met | Ser | Asp | Val | Tyr | Asn | Asn | Pro | Val | Leu | Lys | Phe | Gln | Lys |
|     |     |     |     | 85  |     |     |     |     | 90  |     |     |     |     | 95  |     |
| Lys | Tyr | Ala | Val | Pro | Leu | Ile | Gly | Thr | Val | Cys | Phe | Ala | Leu | Pro | Thr |
|     |     |     | 100 |     |     |     |     | 105 |     |     |     |     | 110 |     |     |
| Leu | Ile | Pro | Val | Tyr | Cys | Trp | Gly | Glu | Ser | Trp | Asn | Asn | Ala | Trp | His |
|     |     | 115 |     |     |     |     | 120 |     |     |     |     | 125 |     |     |     |
| Ile | Ala | Leu | Phe | Arg | Tyr | Ile | Phe | Asn | Leu | Asn | Val | Thr | Phe | Leu | Val |
|     | 130 |     |     |     |     | 135 |     |     |     |     | 140 |     |     |     |     |
| Asn | Ser | Ala | Ala | His | Ile | Trp | Gly | Asn | Lys | Pro | Tyr | Asp | Lys | Ser | Ile |
| 145 |     |     |     |     | 150 |     |     |     |     | 155 |     |     |     |     | 160 |
| Leu | Pro | Ala | Gln | Asn | Leu | Leu | Val | Ser | Phe | Leu | Ala | Ser | Gly | Glu | Gly |
|     |     |     |     | 165 |     |     |     |     | 170 |     |     |     |     | 175 |     |
| Phe | His | Asn | Phe | His | His |     |     |     |     |     |     |     |     |     |     |
|     |     |     | 180 |     |     |     |     |     |     |     |     |     |     |     |     |

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:6:

| Pro | Ala | Gln | Asn | His | Lys | Leu | Ile | Trp | Pro |
|---|---|---|---|---|---|---|---|---|---|
| 1   |     |     |     | 5   |     |     |     |     | 10  |

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:7:

| Ser | Thr | Glu | Asp | Arg | Arg | Met | Val | Tyr | Gln |
|---|---|---|---|---|---|---|---|---|---|
| 1   |     |     |     | 5   |     |     |     |     | 10  |

( 2 ) INFORMATION FOR SEQ ID NO:8:

( i ) SEQUENCE CHARACTERISTICS:
        ( A ) LENGTH: 1047 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

```
ATGGCTGTGA TGGCACAAAC AGTTCAAGAA ACGGCTACAG TGTTGGAAGA GGAAGCTCGC        60
ACGATGACTC TAGTTGCTCC AAAGACAACG CCAAGGAAAT ATAAATATAT ATACACCAAC       120
```

| | | | | | | |
|---|---|---|---|---|---|---|
| TTTCTTACAT | TTTCATATGC | GCATCTAGCT | GCATTATACG | GACTTTATTT | GAGCTTCACC | 180 |
| TCTGCGAAAT | GGGAAACATT | GCTATTCACT | TTCGTACTCT | TCCACATGTC | AAATATAGGC | 240 |
| ATCACCGCAG | GGGCTCACCG | ACTCTGGACT | CACAAGACTT | TCAAAGCCAA | ATTGCCTTTG | 300 |
| GAAATTGTCC | TCATGATATT | CAACTCTTTA | GCTTTTCAAA | ACACGGCTAT | TACCTGGGCT | 360 |
| AGAGAACATC | GGCTACATCA | CAAATACAGC | GATACTGATG | CTGATCCCCA | CAATGCGTCA | 420 |
| AGAGGGTTCT | TCTACTCGCA | TGTTGGCTGG | CTATTAGTAA | AAAAACATCC | CGACGTCCTG | 480 |
| AAATATGGAA | AAACTATAGA | CATGTCGGAT | GTATACAATA | ATCCTGTGTT | AAAATTTCAG | 540 |
| AAAAGTACG | CAGTACCCTT | AATTGGAACA | GTTTGTTTTG | CTCTTCCAAC | TTTGATTCCA | 600 |
| GTCTACTGTT | GGGGCGAATC | GTGGAACAAC | GCTTGGCACA | TAGCCTTATT | TCGATACATA | 660 |
| TTCAATCTTA | ACGTGACTTT | CCTAGTCAAC | AGTGCTGCGC | ATATCTGGGG | GAATAAGCCT | 720 |
| TATGATAAAA | GCATCTTGCC | CGCTCAAAAC | CTGCTGGTTT | CCTTCCTAGC | AAGTGGAGAA | 780 |
| GGCTTCCATA | ATTACCATCA | CGTCTTTCCA | TGGGATTACC | GCACAGCAGA | ATTAGGGAAT | 840 |
| AACTTCCTGA | ATTTGACGAC | GCTGTTCATT | GATTTTGTG | CCTGGTTTGG | ATGGGCGTAT | 900 |
| GACTTGAAGT | CTGTATCAGA | GGATATTATA | AACAGAGAG | CTGAACGAAC | AGGTGACGGT | 960 |
| TCTTCAGGGG | TCATTTGGGG | ATGGACGAC | AAAGACATGG | ACCGCGATAT | AAAATCTAAA | 1020 |
| GCTAACATTT | TTTATGCTAA | AAAGGAA | | | | 1047 |

(2) INFORMATION FOR SEQ ID NO:9:

(i) SEQUENCE CHARACTERISTICS:
        (A) LENGTH: 546 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

| | | | | | | |
|---|---|---|---|---|---|---|
| CAYCRNCTST | GGWCNCAYAA | GACTTTCAAA | GCCAAATTGC | CTTTGGAAAT | TGTCCTCATG | 60 |
| ATATTCAACT | CTTTAGCTTT | TCAAAACACG | GCTATTACCT | GGGCTAGAGA | ACATCGGCTA | 120 |
| CATCACAAAT | ACAGCGATAC | TGATGCTGAT | CCCCACAATG | CGTCAAGAGG | GTTCTTCTAC | 180 |
| TCGCATGTTG | GCTGGCTATT | AGTAAAAAAA | CATCCCGACG | TCCTGAAATA | TGGAAAAACT | 240 |
| ATAGACATGT | CGGATGTATA | CAATAATCCT | GTGTTAAAAT | TTCAGAAAAA | GTACGCAGTA | 300 |
| CCCTTAATTG | GAACAGTTTG | TTTTGCTCTT | CCAACTTTGA | TTCCAGTCTA | CTGTTGGGGC | 360 |
| GAATCGTGGA | ACAACGCTTG | GCACATAGCC | TTATTTCGAT | ACATATTCAA | TCTTAACGTG | 420 |
| ACTTTCCTAG | TCAACAGTGC | TGCGCATATC | TGGGGAATA | AGCCTTATGA | TAAAAGCATC | 480 |
| TTGCCCGCTC | AAAACCTGCT | GGTTTCCTTC | CTAGCAAGTG | GAGAAGGCTT | CCATAAYTWC | 540 |
| CAYCAC | | | | | | 546 |

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

| | | |
|---|---|---|
| CCCCAYCRNC | TSTGGWCNCA | Y | 21 |

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

CCCTCTAGAR TGRTGRWART TRTGRWA 27

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:12:

His Asn Tyr His His
1               5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:13:

His Arg Leu Trp Thr His
1               5

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:14:

His Arg Leu Trp Ser His
1               5

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:15:

His Asn Tyr His His Tyr
1               5

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:16:

```
His  Asn  Tyr  His  His  Phe
1                   5
```

( 2 ) INFORMATION FOR SEQ ID NO:17:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:17:

```
His  Asn  Phe  His  His  Tyr
1                   5
```

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:18:

```
His  Asn  Phe  His  His  Phe
1                   5
```

( 2 ) INFORMATION FOR SEQ ID NO:19:

( i ) SEQUENCE CHARACTERISTICS:
        ( A ) LENGTH: 358 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:19:

```
Met  Pro  Ala  His  Met  Leu  Gln  Glu  Ile  Ser  Ser  Ser  Tyr  Thr  Thr  Thr
1                   5                        10                      15

Thr  Thr  Ile  Thr  Glu  Pro  Pro  Ser  Gly  Asn  Leu  Gln  Asn  Gly  Arg  Glu
               20                       25                      30

Lys  Met  Lys  Lys  Val  Pro  Leu  Tyr  Leu  Glu  Glu  Asp  Ile  Arg  Pro  Glu
          35                       40                  45

Met  Arg  Glu  Asp  Ile  His  Asp  Pro  Ser  Tyr  Gln  Asp  Glu  Glu  Gly  Pro
     50                       55                  60

Pro  Pro  Lys  Leu  Glu  Tyr  Val  Trp  Arg  Asn  Ile  Ile  Leu  Met  Ala  Leu
65                       70                  75                           80

Leu  His  Val  Gly  Ala  Leu  Tyr  Gly  Ile  Thr  Leu  Ile  Pro  Ser  Ser  Lys
                    85                       90                      95

Val  Tyr  Thr  Leu  Leu  Trp  Gly  Ile  Phe  Tyr  Tyr  Leu  Ile  Ser  Ala  Leu
               100                      105                     110
```

```
Gly  Ile  Thr  Ala  Gly  Ala  His  Arg  Leu  Trp  Ser  His  Arg  Thr  Tyr  Lys
          115                      120                     125

Ala  Arg  Leu  Pro  Leu  Arg  Ile  Phe  Leu  Ile  Ile  Ala  Asn  Thr  Met  Ala
          130                      135                     140

Phe  Gln  Asn  Asp  Val  Tyr  Glu  Trp  Ala  Arg  Asp  His  Arg  Ala  His  His
145                           150                     155                     160

Lys  Phe  Ser  Glu  Thr  His  Ala  Asp  Pro  His  Asn  Ser  Arg  Arg  Gly  Phe
                    165                     170                     175

Phe  Phe  Ser  His  Val  Gly  Trp  Leu  Leu  Val  Arg  Lys  His  Pro  Ala  Val
               180                      185                     190

Lys  Glu  Lys  Gly  Gly  Lys  Leu  Asp  Met  Ser  Asp  Leu  Lys  Ala  Glu  Lys
          195                      200                     205

Leu  Val  Met  Phe  Gln  Arg  Arg  Tyr  Tyr  Lys  Pro  Gly  Leu  Leu  Leu  Met
     210                      215                     220

Cys  Phe  Ile  Leu  Pro  Thr  Leu  Val  Pro  Trp  Tyr  Cys  Trp  Gly  Glu  Thr
225                           230                     235                     240

Phe  Leu  His  Ser  Leu  Phe  Val  Ser  Thr  Phe  Leu  Arg  Tyr  Thr  Leu  Val
                    245                     250                     255

Leu  Asn  Ala  Thr  Trp  Leu  Val  Asn  Ser  Ala  Ala  His  Leu  Tyr  Gly  Tyr
               260                      265                     270

Arg  Pro  Tyr  Asp  Lys  Asn  Ile  Gln  Ser  Arg  Glu  Asn  Ile  Leu  Val  Ser
          275                      280                     285

Leu  Gly  Ser  Val  Gly  Glu  Gly  Phe  His  Asn  Tyr  His  His  Ala  Phe  Pro
     290                      295                     300

Tyr  Asp  Tyr  Ser  Ala  Ser  Glu  Tyr  Arg  Trp  His  Ile  Asn  Phe  Thr  Thr
305                           310                     315                     320

Phe  Phe  Ile  Asp  Cys  Met  Ala  Ala  Leu  Gly  Leu  Ala  Tyr  Asp  Arg  Lys
               325                      330                     335

Lys  Val  Ser  Lys  Ala  Ala  Val  Leu  Ala  Arg  Ile  Lys  Arg  Thr  Gly  Asp
               340                      345                     350

Gly  Ser  His  Lys  Ser  Ser
               355
```

PHEROMONE DESATURASES

This work was supported by National Science foundation Grant No. IBN-9004979. The Federal Government may retain certain rights in the invention.

FIELD OF THE INVENTION

The present invention relates to desaturases and, more particularly, to desaturases expressed in insect pheromone glands.

BACKGROUND OF THE INVENTION

Since the advent of DDT more than 50 years ago, broad-spectrum neurotoxic insecticides have provided the principal means for the control of economically important insects in agriculture and public health programs. Whereas the use of synthetic insecticides initially resulted in spectacular increases in crop yields and the suppression of some important human and animal disease vectors, the development of insecticide resistance in insect pest populations and the environmental damage caused by insecticides have become widely recognized as serious drawbacks to their use. Among the most significant environmental problems associated with the manufacture and use of insecticides are 1) their direct toxicity to nontarget organisms (including humans); 2) their persistence in the biosphere where they can accumulate and cause untoward developmental and reproductive effects in higher organisms; 3) significant point-source pollution associated with their manufacture and distribution; 4) their worldwide dispersal.

Because of these problems there have been considerable government, industry, and academic efforts to develop and implement integrated pest management ("IPM") approaches employing less toxic alternatives for insect control. Such IPM strategies typically combine several pest control techniques including better controlled and reduced applications of more specific and less persistent conventional insecticides; cultural practices; development of host plant resistance; use of "biologicals" such as predatory or parasitic insects, pathogenic bacteria, and viruses, and use of insect sex pheromones.

Many insects communicate via the release of volatile chemicals known as pheromones. Sex pheromones, for example, are typically released by the female insect at appropriate times to attract males of the same species for mating. The latter phenomenon has been exploited to prevent insect mating (and consequently reduce insect populations) by releasing sufficient quantities of synthetically produced pheromone in the field to effectively impair the ability of males to find and mate with females. Pheromones have been used in this way on a commercial basis for about 15 years, and have been shown to provide effective control for numerous insect pest species, especially Lepidopteran species (moths). Among these are the pink bollworm (*Pectinophora gossypiella*) in cotton, codling moth (*Cydia pomonella*) in apples, pears, and walnuts, oriental fruit moth (*Grapholitha molesta*) in peaches and nectarines, tomato pinworm (*Keifera lycopersicella*) in tomatoes, grape berry moth (*Endopiza viteana*) in grapes, artichoke plum moth (*Platyptilia carduidactyla*) in artichokes, beet armyworm (*Spodoptera exigua*) in onions and other vegetables, rice stem borer (*Chilo supressalis*) in rice, and Mexican rice borer (*Eoreuma loftini*) in sugar cane.

The commercial use of pheromones to control insect pests by mating disruption has several advantages over conventional insecticides. Pheromones are: 1) nontoxic and environmentally benign; 2) specific to one target species and do not adversely affect nontarget beneficial insects, making them extremely well suited for use in IPM programs; 3) much less likely (and have never been shown) to produce resistance in the target insect; and 4) registered for use much more easily than are conventional insecticides, typically requiring 2–4 years and less than $500,000, compared to 8–10 years and over $40 million for conventional insecticides.

Despite the many advantages pheromones exhibit over insecticides, their market penetration has been slow: the total U.S. market for pheromone-based mating disruption products was reported to be only $32 million in 1989, vs. the $6 billion worldwide annual insecticide market. The principal reason for this is that pheromones are at best only cost-competitive with insecticides. Most insect pheromones cost between $350/kg and $3,000/kg, with the pink bollworm pheromone being the most commercially advanced pheromone product on the market at $350/kg. The weekly cost of controlling pink bollworm in cotton with either pheromones or insecticides is the same: about $6–8/acre. Because more than half of the cost of pheromone products are attributable to their synthesis, and, in view of the importance of market factors governing the acceptance of pheromones for insect control, substituting less expensive enzymatically mediated steps for conventional chemical steps to reduce production cost should result in increased pheromone use.

Most insect sex pheromones are aliphatic compounds having a specific location of unsaturation and a terminal alcohol, acetate, or aldehyde functional group. These compounds are enzymatically synthesized in vivo from readily available saturated fatty acid precursors (Roelofs, et al. "Pheromone Biosynthesis in the Lepidoptera," *J. Chem. Ecol.* 14:2019–2031 (1988)).

In contrast to pheromone syntheses in nature, current approaches for the commercial production of pheromones employ traditional synthetic chemical routes. Because pheromones require very high purity to elicit an insect's response, these syntheses are expensive and difficult. In general, coupling reactions that use moisture- and oxygen-sensitive organometallic reagents are required to establish the correct position of the double bond. These coupling reactions require elaborate manipulations and especially pure feedstocks and solvents, and generate large amounts of organic wastes that require treatment.

Thus, the coupling reactions typically drive the cost of the process. Moreover, since pheromones are effective in such small quantities (typically a few grams per acre), the cost of pheromone production via standard techniques is unlikely to decrease significantly from volume production. It is, therefore, expected that the costs of chemical starting materials and intermediates will remain high, as is typically the case in the specialty chemicals industry, unless these high value intermediates can be formed directly from inexpensive starting materials.

For these and other reasons, there remains a need for a method for forming high value pheromone intermediates from inexpensive starting materials.

SUMMARY OF INVENTION

The present invention relates to an isolated membrane-associated acyl-CoA desaturase expressed in the pheromone gland of an insect. The isolated desaturase of the present invention can be used to produce a pheromone precursor by converting a saturated or unsaturated fatty acyl-CoA reactant to an unsaturated fatty acyl-CoA product. The fatty acyl-CoA product contains at least one more carbon-carbon double bond than the fatty acyl-CoA reactant.

The present invention also relates to an isolated DNA molecule encoding a membrane-associated acyl-CoA desaturase expressed in the pheromone gland of an insect. The molecule can be inserted as a heterologous (i.e., not naturally present) DNA expression system for producing the desaturase of the present invention. Likewise, the heterologous DNA, usually inserted in an expression vector to form a recombinant DNA expression system, can be incorporated in a host cell to express the protein.

In addition, the present invention relates to methods for producing an unsaturated fatty acyl-CoA product. One method includes providing an isolated membrane-associated acyl-CoA desaturase of the present invention and converting a saturated or unsaturated fatty acyl-CoA reactant to an unsaturated fatty acyl-CoA product using the desaturase. The unsaturated fatty acyl-CoA product contains at least one more carbon-carbon double bond than the fatty acyl-CoA reactant. In one embodiment, a host cell transformed with an expression system comprising a DNA molecule of the present invention is cultured under conditions effective to produce the unsaturated fatty acyl-CoA product. Another embodiment includes providing a host olel cell transformed with an expression system and culturing the host cell under conditions effective to produce the unsaturated fatty acyl-CoA product. In this method, the expression system used to transform the host cell includes a yeast OLE1 Δ9 acyl-CoA desaturase gene having a modification of the coding region such that its central portion, which encodes the catalytic domain of the OLE1 Δ9 acyl-CoA desaturase, is replaced with a DNA molecule encoding a catalytic domain of a membrane associated acyl CoA desaturase expressed in the pheromone gland of an insect.

BRIEF DESCRIPTION OF THE DRAWINGS

FIG. 4 depicts the conserved amino acid sequences of Δ9 desaturases of rat (Ratdesat, SEQ. ID. No. 19) and yeast (Ole1desat, SEQ. ID. No. 20) used in designing degenerate PCR primers as described in Example 4. Conserved amino acid sequences are underlined.

FIG. 5 is the nucleotide sequence (SEQ. ID. No. 9) of the PCR product amplified from *T. ni* pheromone gland generated by 5'Δ9d1 and 3'Δ9d2 Primers as described in Example 5. The underlined sequences derived from the PCR primers and are not necessarily reflective of the corresponding regions present in the genomic DNA.

FIG. 6 is the amino acid sequence (SEQ. ID. No. 5) encoded by the nucleotide sequence of the PCR product amplified from *T. ni* pheromone gland generated by 5'Δ9d1 and 3'Δ9d2 Primers as described in Example 5.

FIG. 7 is the full-length nucleotide sequence of the coding region of the *T. ni* Δ11 desaturase cDNA (SEQ. ID. No. 8).

FIG. 8 depicts the full-length amino acid sequence of *T. ni* Δ11 desaturase (SEQ. ID. No. 4).

FIG. 9 presents the amino acid sequence of the protein encoded by the cabbage looper moth *T. ni* pheromone gland-specific cDNA compared to sequences of Δ9 desaturases of rat (Ratdesat, SEQ. ID. No. 19) and yeast (Ole1desat, SEQ. ID. No. 20). Numbering begins at the first Met residue of the yeast sequence. Overlined regions are the conserved sites to which the degenerate target primers were designed.

FIG. 10 presents the hydrophobicity plots of the *T. ni* Δ11 desaturase, rat Δ9 desaturase, and yeast Δ9 desaturase discussed in Example 6.

DETAILED DESCRIPTION

Figure 1:
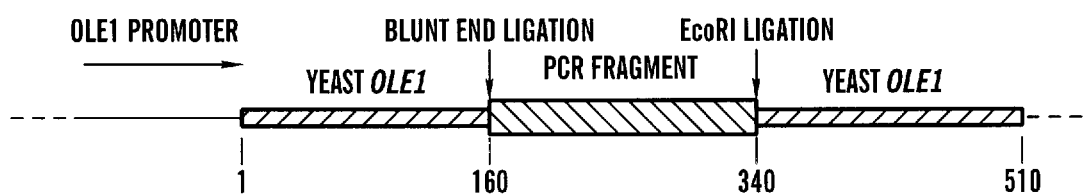
FIG. 1 is a diagram depicting a hybrid desaturase expression construct useful in the cassette cloning procedure of the present invention. Numbers correspond to yeast amino acid residues. The dashed lines represent vector sequence.

The present invention relates to an isolated membrane-associated desaturase expressed in the pheromone gland of an insect. Although the invention is not limited to any particular insect, those insect species from the moth (Lepidoptera) family, such as the cabbage looper moth (*Trichoplusia ni*), pink bollworm (*Pectinophora gossypiella*), codling moth (*Cydia pomonella*), oriental fruit moth (*Grapholitha molesta*), tomato pinworm (*Keifera lycopersicella*), grape berry moth (*Endopiza viteana*), artichoke plum moth (*Platyptilia carduidactyla*), beet armyworm (*Spodoptera exigua*), rice stem borer (*Chilo supressalis*), Mexican rice borer (Eoreuma loftini), leafroller moth (*Plantoitrix excessana*), Asian cornborer (*Ostrinia furnacalis*), potato tuberworm moth (*Phthorimaea operculella*), potato tuber moth (*Scrobipalpopsis solanivora*), tobacco stem borer moth (*Scrobipalpa heliopa*), sugar beet moth (*Scrobipalpa ocellatella*), and tomato moth (*Scrobipalpuloides absoluta*) are particularly contemplated. Desaturases within the scope of the present invention include Δ9, Δ10, Δ11, Δ12, and Δ14 acyl-CoA desaturases which are membrane-associated and expressed in the insect pheromone gland. The invention further includes desaturases which produce either the Z or the less common E isomer.

One particularly useful desaturase is the Δ11 desaturase, such as the *T. ni* Δ11 desaturase. This isolated protein, *T. ni* Δ11 desaturase, has a molecular weight (as calculated from the isolated *T. ni* Δ11 desaturase's amino acid sequence) from about 39 to about 42 kDa and a isoelectric point (as calculated from the isolated *T. ni* Δ11 desaturase's amino acid sequence) from about 8.9 to about 9.0.

Without intending to be limited by the following explanation, it is believed that membrane-bound acyl-CoA desaturases contain three regions of conserved histidine-containing primary sequence. Specifically, the first two of these regions, having $HX_4H$ (SEQ. ID. No. 1) and $HX_2HH$ (SEQ. ID. No. 2) motifs, respectively, separated by from 20 to 40 amino acid residues. The third region, having a $HX_2HH$ motif, is separated from the $HX_2HH$ motif of the second region by from about 125 to about 145 residues. More specifically, membrane-associated acyl-CoA desaturases comprising the following consensus sequence:

are encompassed in the scope of the present invention. Illustrative membrane-associated desaturases of the present invention include those comprising the following amino acid sequences (SEQ. ID. No. 3)

$$HX_4HX_{30}HX_2HHX_{135}HX_2HH$$

Membrane-associated acyl-CoA desaturases of the present invention include those having an amino acid sequences comprising histidine residues at each of the following positions: n, n+5, n+37, n+40, n+41, n+178, n+180, and n+181. As used above, n is an integer, H is a histidine residue, and X designates an amino acid residue.

In another embodiment, this aspect of the present invention relates to isolated proteins or polypeptides having an amino acid sequence corresponding to SEQ. ID. No. 4, as follows:

Met Ala Val Met Ala Gln Thr Val Gln Glu Thr Ala Thr Val

Leu Glu Glu Glu Ala Arg Thr Met Thr Leu Val Ala Pro Lys

Thr Thr Pro Arg Lys Tyr Lys Tyr Ile Tyr Thr Asn Phe Leu

Thr Phe Ser Tyr Ala His Leu Ala Ala Leu Tyr Gly Leu Tyr

Leu Ser Phe Thr Ser Ala Lys Trp Glu Thr Leu Leu Phe Thr

Phe Val Leu Phe His Met Ser Asn Ile Gly Ile Thr Ala Gly

Ala His Arg Leu Trp Thr His Lys Thr Phe Lys Ala Lys Leu

Pro Leu Glu Ile Val Leu Met Ile Phe Asn Ser Leu Ala Phe

Gln Asn Thr Ala Ile Thr Trp Ala Arg Glu His Arg Leu His

His Lys Tyr Ser Asp Thr Asp Ala Asp Pro His Asn Ala Ser

Arg Gly Phe Phe Tyr Ser His Val Gly Trp Leu Leu Val Lys

Lys His Pro Asp Val Leu Lys Tyr Gly Lys Thr Ile Asp Met

Ser Asp Val Tyr Asn Asn Pro Val Leu Lys Phe Gln Lys Lys

Tyr Ala Val Pro Leu Ile Gly Thr Val Cys Phe Ala Leu Pro

Thr Leu Ile Pro Val Tyr Cys Trp Gly Glu Ser Trp Asn Asn

Ala Trp His Ile Ala Leu Phe Arg Tyr Ile Phe Asn Leu Asn

Val Thr Phe Leu Val Asn Ser Ala Ala His Ile Trp Gly Asn

Lys Pro Tyr Asp Lys Ser Ile Leu Pro Ala Gln Asn Leu Leu

Val Ser Phe Leu Ala Ser Gly Glu Gly Phe His Asn Tyr His

His Val Phe Pro Trp Asp Tyr Arg Thr Ala Glu Leu Gly Asn

Asn Phe Leu Asn Leu Thr Thr Leu Phe Ile Asp Phe Cys Ala

Trp Phe Gly Trp Ala Tyr Asp Leu Lys Ser Val Ser Glu Asp

Ile Ile Lys Gln Arg Ala Glu Arg Thr Gly Asp Gly Ser Ser

Gly Val Ile Trp Gly Trp Asp Asp Lys Asp Met Asp Arg Asp

Ile Lys Ser Lys Ala Asn Ile Phe Tyr Ala Lys Lys Glu

In another embodiment, this aspect of the present invention relates to isolated proteins or polypeptides having an amino acid sequence corresponding to SEQ. ID. No. 5, as follows:

His Arg Leu Trp Ser His Lys Thr Phe Lys Ala Lys Leu Pro

Leu Glu Ile Val Leu Met Ile Phe Asn Ser Leu Ala Phe Gln

Asn Thr Ala Ile Thr Trp Ala Arg Glu His Arg Leu His His

Lys Tyr Ser Asp Thr Asp Ala Asp Pro His Asn Ala Ser Arg

Gly Phe Phe Tyr Ser His Val Gly Trp Leu Leu Val Lys Lys

His Pro Asp Val Leu Lys Tyr Gly Lys Thr Ile Asp Met Ser

Asp Val Tyr Asn Asn Pro Val Leu Lys Phe Gln Lys Lys Tyr

Ala Val Pro Leu Ile Gly Thr Val Cys Phe Ala Leu Pro Thr

Leu Ile Pro Val Tyr Cys Trp Gly Glu Ser Trp Asn Asn Ala

Trp His Ile Ala Leu Phe Arg Tyr Ile Phe Asn Leu Asn Val

Thr Phe Leu Val Asn Ser Ala Ala His Ile Trp Gly Asn Lys

Pro Tyr Asp Lys Ser Ile Leu Pro Ala Gln Asn Leu Leu Val

Ser Phe Leu Ala Ser Gly Glu Gly Phe His Asn Phe His His

The present invention also relates to desaturases which have greater than about 90% identity with respect to the above-described amino acid sequence, provided that the desaturases contain the three regions of conserved histidine containing motifs. The present invention also relates to acyl-CoA desaturases which have greater than about 90% similarity with respect to the above-described amino acid sequence. In this context, a protein is 90% similar to the above-described amino acid sequence when 90% of the amino acid residues in the protein are the same as or conservative substitutions of the residues of the above-described amino acid sequence. As used herein, two amino acid residues are conservative substitutions of one another where the two residues are of the same type. In this regard, for purposes of the present invention, proline, alanine, glycine, serine, and threonine, all of which are neutral, weakly hydrophobic residues, are of the same type. Glutamine, glutamic acid, asparagine, and aspartic acid, all of which are acidic, hydrophilic residues, are of the same type. Another type of residue is the basic, hydrophilic amino acid residues, which include histidine, lysine, and arginine. Leucine, isoleucine, valine, and methionine all of which are hydrophobic, aliphatic amino acid residues, form yet another type of residue. Yet another type of residue consists of phenylalanine, tyrosine, and tryptophan, all of which are hydrophobic, aromatic residues. For example, the sequence PAQNHKLIWP (SEQ. ID. No. 6) is 90% similar to STEDRRMVYQ (SEQ. ID. No. 7).

The desaturases of the present invention can be isolated. That is, they are not mixed with, or are present in much greater concentrations relative to, the biological materials with which they are typically found when they occur naturally, for example, in the cells of the pheromone gland. Optionally, the desaturases of the present invention can be purified, that is substantially free of biological materials, such as other proteins, peptides, polysaccharides, cells, cellular debris, and the like.

Another aspect of the present invention relates to a DNA molecule encoding a protein or polypeptide of the present invention. In particular, the invention relates to a DNA molecule encoding a membrane-associated acyl-CoA desaturase expressed in the pheromone glands of an insect, such as a moth. DNA molecules encoding Δ11 desaturases or those encoding desaturases expressed in the pheromone gland of a *T. ni* moth are particularly useful. As to the Δ11 desaturase of the *T. ni* moth, the DNA molecule comprises a nucleotide sequence which encodes a protein having an amino acid sequence corresponding to SEQ. ID. No. 4. In particular, the invention relates to a DNA molecule comprising a nucleotide sequence corresponding to SEQ. ID. No. 8, as follows:

```
ATG GCT GTG ATG GCA CAA ACA GTT CAA GAA ACG GCT ACA GTG

TTG GAA GAG GAA GCT CGC ACG ATG ACT CTA GTT GCT CCA AAG

ACA ACG CCA AGG AAA TAT AAA TAT ATA TAC ACC AAC TTT CTT

ACA TTT TCA TAT GCG CAT CTA GCT GCA TTA TAC GGA CTT TAT

TTG AGC TTC ACC TCT GCG AAA TGG GAA ACA TTG CTA TTC ACT

TTC GTA CTC TTC CAC ATG TCA AAT ATA GGC ATC ACC GCA GGG

GCT CAC CGA CTC TGG ACT CAC AAG ACT TTC AAA GCC AAA TTG

CCT TTG GAA ATT GTC CTC ATG ATA TTC AAC TCT TTA GCT TTT

CAA AAC ACG GCT ATT ACC TGG GCT AGA GAA CAT CGG CTA CAT

CAC AAA TAC AGC GAT ACT GAT GCT GAT CCC CAC AAT GCG TCA

AGA GGG TTC TTC TAC TCG CAT GTT GGC TGG CTA TTA GTA AAA

AAA CAT CCC GAC GTC CTG AAA TAT GGA AAA ACT ATA GAC ATG

TCG GAT GTA TAC AAT AAT CCT GTG TTA AAA TTT CAG AAA AAG

TAC GCA GTA CCC TTA ATT GGA ACA GTT TGT TTT GCT CTT CCA

ACT TTG ATT CCA GTC TAC TGT TGG GGC GAA TCG TGG AAC AAC

GCT TGG CAC ATA GCC TTA TTT CGA TAC ATA TTC AAT CTT AAC

GTG ACT TTC CTA GTC AAC AGT GCT GCG CAT ATC TGG GGG AAT

AAG CCT TAT GAT AAA AGC ATC TTG CCC GCT CAA AAC CTG CTG

GTT TCC TTC CTA GCA AGT GGA GAA GGC TTC CAT AAT TAC CAT

CAC GTC TTT CCA TGG GAT TAC CGC ACA GCA GAA TTA GGG AAT

AAC TTC CTG AAT TTG ACG ACG CTG TTC ATT GAT TTT TGT GCC

TGG TTT GGA TGG GCG TAT GAC TTG AAG TCT GTA TCA GAG GAT
```

-continued
```
ATT ATA AAA CAG AGA GCT GAA CGA ACA GGT GAC GGT TCT TCA

GGG GTC ATT TGG GGA TGG GAC GAC AAA GAC ATG GAC CGC GAT

ATA AAA TCT AAA GCT AAC ATT TTT TAT GCT AAA AAG GAA
```

Another embodiment of the present invention relates to a DNA molecule which encodes a fragment of an acyl-CoA desaturase protein delimited by the two regions of conserved histidine-containing primary amino acid sequence described above. One exemplary set of such DNA molecules are those DNA molecules encoding a protein having an amino acid sequence corresponding to SEQ. ID. No. 5. In particular, the present invention relates to a DNA molecule comprising a nucleotide sequence corresponding to SEQ. ID. No. 9, as follows:

```
CAY CRN CTS TGG WCN CAY AAG ACT TTC AAA GCC AAA TTG CCT

TTG GAA ATT GTC CTC ATG ATA TTC AAC TCT TTA GCT TTT CAA

AAC ACG GCT ATT ACC TGG GCT AGA GAA CAT CGG CTA CAT CAC

AAA TAC AGC GAT ACT GAT GCT GAT CCC CAC AAT GCG TCA AGA

GGG TTC TTC TAC TCG CAT GTT GGC TGG CTA TTA GTA AAA AAA

CAT CCC GAC GTC CTG AAA TAT GGA AAA ACT ATA GAC ATG TCG

GAT GTA TAC AAT AAT CCT GTG TTA AAA TTT CAG AAA AAG TAC

GCA GTA CCC TTA ATT GGA ACA GTT TGT TTT GCT CTT CCA ACT

TTG ATT CCA GTC TAC TGT TGG GGC GAA TCG TGG AAC AAC GCT

TGG CAC ATA GCC TTA TTT CGA TAC ATA TTC AAT CTT AAC GTG

ACT TTC CTA GTC AAC AGT GCT GCG CAT ATC TGG GGG AAT AAG

CCT TAT GAT AAA AGC ATC TTG CCC GCT CAA AAC CTG CTG GTT

TCC TTC CTA GCA AGT GGA GAA GGC TTC CAT AAY TWC CAY CAC
```

As used herein, Y indicates a nucleotide selected from cytosine and thymine; W indicates a nucleotide selected from adenine and thymine; R indicates a nucleotide selected from adenine and guanine; S indicates a nucleotide selected from cytosine and guanine; and N indicates a nucleotide selected from cytosine, adenine, guanine, and thymine.

The DNA molecules of the present invention can be isolated using polymerase chain reaction ("PCR") based homology probing as described by Gould et al., Proc. Nat'l. Acad. Sci. USA 86:1934–1938 (1989), Kamb et al., Proc. Nat'l. Acad. Sci. USA 86:4372–4376 (1989), Doyle et al., Insect Biochem. 21:689–696 (1991), Knipple et al., Arch. Insect Biochem. Physiol. 16:45–53 (1991), Knipple et al., "Isolation of insect genes coding for voltage-sensitive sodium channels and ligand-gated chloride channels by PCR-based homology probing," in Neurotox '91, Molecular Basis of Drug and Pesticide Action, Duce, ed., Essex, UK: Elsevier Science Publishers pp. 271–283 (1992), Henderson et al., Biochem. Biophysic. Res. Comm. 193:474–482 (1993), and Henderson et al., Insect Biochem. Molec. Biol. 24:363–371 (1994), which are hereby incorporated by reference.

Briefly, pheromone glands are removed, such as by dissection, from a developmental stage when pheromone biosynthesis is underway. For example, in the cabbage looper moth, pheromone glands are dissected from adult female moths or pupae, preferably from newly eclosed (0–12 hour) adults. mRNA from these glands is then purified, such as by extraction with an acid quanidinum isothiocyanate-phenol-chloroform extraction buffer in accordance with the method of Chomczynski, Anal. Biochem. 162:156–159 (1987), which is hereby incorporated by reference. The procedure typically produces yields of about 200 $\mu$g of total RNA from 1000 extirpated glands, which, upon hybrid-selection with a synthetic oligonucleotide comprising a homo-oligomer of thymidine ("oligo-dT") attached to any of various sold phase supports produces about 5 $\mu$g of intact poly-A+-RNA. The poly A+-RNA thus produced is then used as a template in reverse transcription reactions to make cDNA which, in turn, is used either directly as a template in PCR reactions or as template for constructing cDNA libraries of the insect pheromone gland by ligation into any suitable cloning vector. Suitable cDNA libraries can be constructed, for example, using oligo-dT or random hexamers in an appropriate cloning vector, such as by the method described in Tang et al., "Construction of a cDNA Library from Cabbage Looper Moth Sex Pheromone Gland," In *Molecular Insect Science*, Hagedorn et al., eds., New York: Plenum, p. 368 (1990), which is hereby incorporated by reference.

To amplify acyl-CoA desaturase-encoding gene sequences, appropriate primers, designed according to the amino acid sequences of the two conserved histidine-containing primary sequence regions, described above, are used in PCR reactions containing insect pheromone gland cDNA or DNA obtained from cDNA libraries, such as described above. Appropriate primers include those having a nucleotide sequence corresponding to SEQ. ID. No. 10, as follows:

CCC CAY CRN CTS TGG WCN CAY

SEQ. ID. No. 11, as follows:

CCC TCTAGA RTG RTG RWA RTT RTG RWA.

These mixed sequence primer pools (or "degenerate primers") contain all possible nucleotide sequences encoding the conserved amino acid sequence motif of the pheromone gland-specific acyl-CoA desaturase. Less degenerate subsets of the above primer sequences that, for example, take into account codon bias or simply chance match with the target sequence can also be employed. Similarly, additional sequence possibilities can be employed by taking into account nucleotide substitutions that permit more than one amino acid sequence to be specified, for example, where a position is not conserved in the target sequence or where any conservative amino acid substitution is possible.

The sequences amplified by the above primers correspond to a portion of the desaturase coding region which is delimited by the two conserved histidine-containing motifs targeted by the degenerate primers. In some instances more than one unique sequence may be obtained since multiple desaturases exist in the pheromone glands of many species of insects. In such cases, identification of each unique desaturase-encoding sequence can be effected by subcloning the amplification products obtained with the above primers and sequencing several of the clones produced in the subcloning procedure.

Isolation of full length desaturase-encoding cDNAs corresponding to each unique amplification product is then effected by procedures well known to those skilled in the art, such as by standard hybridization screening of pheromone gland cDNA libraries, as described by Sambrook et al., *Molecular Cloning: A Laboratory Manual*, Cold Springs Laboratory, Cold Springs Harbor, N.Y. (1989), which is hereby incorporated by reference. Alternatively, another means to obtain a full length acyl-CoA desaturase-encoding cDNA is by isolating the 5' and 3' ends of the cDNA corresponding to each unique amplification product by the Rapid Amplification of cDNA Ends ("RACE") procedure described by Frohman et al., Technique 1:165–170 (1989), which is hereby incorporated by reference. Sequencing of the full length cDNAs thus isolated can be achieved by any of the conventional methods known in the art, such as by the method of Sanger et al., Proc. Nat. Acad. Sci. USA 74:5463–5467 (1977), which is hereby incorporated by reference. In those species of insect in which multiple desaturases occur, identification of each unique desaturase-encoding sequence can be effected by sequencing several of the clones produced in the above procedures.

The DNA molecule of the present invention can be incorporated in cells using conventional recombinant DNA technology. Generally, this involves inserting the DNA molecule into an expression system to which the DNA molecule is heterologous (i.e., not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/- or KS +/- (see "Stratagene Cloning Systems" Catalog (1993) from Stratagene, La Jolla, Calif., which is hereby incorporated by reference), pQE, pIH821, pGEX, pET series (see Studier et. al., "Use of T7 RNA Polymerase to Direct Expression of Cloned Genes," Gene *Expression Technology* vol. 185 (1990), which is hereby incorporated by reference) and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference.

A variety of host-vector systems may be utilized to express the desaturase-encoding sequence(s) Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus) . The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts, et al., *Methods in Enzymology*, 68:473 (1979), which is hereby incorporated by reference.

Promotors vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG ATG combination produced by recombinant DNA or other techniques involving incorporation of synthetic nucleotides may be used.

Once the isolated DNA molecule of the present invention has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like.

The host cell can then be cultured under conditions which facilitate growth of the cells and expression of the DNA molecule as will be apparent to one skilled in the art, then isolated and purified such as by the procedure described in Strittmatter et al., "Bacterial Synthesis of Active Rat Stearoyl-CoA Desaturase Lacking the 26-residue Amino-terminal Amino Acid Sequence," *J. Biol. Chem.* 263:2532–2555 (1988), which is hereby incorporated by reference. If necessary, the acyl-CoA desaturase-containing fraction may be further purified by standard biochemical methods, well known to those skilled in the art, including chromatography (such as ion exchange, affinity, size exclusion chromatography, and HPLC), centrifugation, or differential solubility.

The present invention also relates to a method for producing an unsaturated fatty acyl-CoA product. The method includes providing an isolated membrane-associated acyl-CoA desaturase of the present invention. The isolated acyl-CoA desaturase is used to convert a saturated or unsaturated fatty acyl-CoA reactant to an unsaturated fatty acyl-CoA product containing at least one more carbon-carbon double bond than the fatty acyl-CoA reactant. Suitable reactants for use in the above method of the present invention include Co-enzyme A thioesters of fatty acids whose hydrocarbon moieties include alkanes, monounsaturated alkenes, or multiunsaturated alkenes, such as alkadienes and alkatrienes. Where the hydrocarbon moiety of the acyl-CoA reactant employed in the practice of this method is an alkene, it, of course, must be saturated (i.e., SP3 hybridized) at the carbons on which the desaturase operates. For example, where a Δn desaturase is employed, the alkene cannot be unsaturated at the n−1, n, or n+1 positions. For example, a Δ11 desaturase can be used to convert an acyl-CoA having an alkene moiety provided that the C10, C11, and C12 carbons are all saturated.

The hydrocarbon moiety of the fatty acyl-CoA reactant can be of any length, preferably from 8 to 20 carbons. Suitable hydrocarbon moieties include octadecyl, heptadecyl, hexadecyl, pentadecyl, tetradecyl, tridecyl, and dodecyl. In addition, unsubstituted alkene moieties, such as octadecenyl, heptadecenyl, hexadecenyl, tetradecenyl, tridecenyl, and dodecenyl, are suitable, provided that the desaturase operates in a region of saturation, as described above. Preferably, the hydrocarbons have an even number of carbons such as 8, 10, 12, 14, 16, 18, or 20. It is thus possible to generate products having multiple double bonds by sequentially using different appropriate desaturases of the present invention.

The position of the carbon-carbon double bond formed and its stereospecificity, i.e., cis (Z) or trans (E), are attributable to the intrinsic properties of the specific insect desaturase provided. The free fatty acid can be readily obtained by de-esterification of the unsaturated acyl-CoA product and further derivatized to produce useful substituted or unsubstituted hydrocarbon compounds.

The mono-, di-, or poly-unsaturated fatty acid products obtained by the methods of the present invention are useful as intermediates for the synthesis of diverse compounds that can be employed as pheromones to attract particular species of insects. The most common types of modifications that can be employed to produce useful pheromone products from unsaturated fatty acid precursors include chain-shortening, chain-elongation, reduction, and esterification. Many of these modifications can be effected by standard organic chemistry methodologies. For example, chemical procedures can be employed for chain elongation, including methods used in conventional pheromone syntheses, for example, Grignard coupling. Aldehydes, alcohols, and acetates are the most commonly occurring functional groups of moth pheromones and these too can be readily obtained by chemical modification of the unsaturated fatty acid products resulting from the present invention. Unsaturated compounds having aldehyde functional group are obtained simply by reduction of unsaturated fatty acid precursors, such as by reacting the latter with lithium in methyl amine. Unsaturated compounds having an alcohol functional group are similarly obtained by reduction of the unsaturated fatty acid with a more powerful reducing agent, such as lithium aluminum hydride in tetrahydrofuran. An acetate functional group can be obtained readily by esterification of the derived alcohol. By means of illustration, these simple chemical reactions can be performed using the (Z)-11-hexadecenoic acid (Z11-16:COOH) product (obtained by conversion of hexadecanoyl-CoA by the $T.$ $ni$ $\Delta 11$ acyl-CoA desaturase of the present invention) as an intermediate for synthesis of two particularly useful products, (Z)-11-hexadecen-1-al (Z11-16:Al) and (Z)-11-hexadecen-1-yl acetate (Z11-16:Ac). The aldehyde derivative is the principal component of the pheromone of the major pest, $Helicoverpa$ $zea$, the corn ear worm. The acetate derivative has been identified as the principal component of the sex pheromones of the major pests, $Heliothis$ $virescens$, the tobacco bud worm, and $Pseudaletia$ $unipuncta$, the true army worm.

Useful modifications of the unsaturated fatty acyl-CoA products of the current invention can also be effected enzymatically either in vivo, for example, in a cell system expressing the desaturase of choice, or in vitro, for example, by incorporating suitable enzymes in a biochemical reactor. Enzymatic activities that mediate chain-shortening by beta-oxidation are particularly useful, since this would permit the position of the double bond to be varied with respect to the carboxylate functional group. In addition, it may be desirable to desaturate further the pheromone precursor as described above, in order to introduce a double bond to obtain an alkadiene precursor. This can be effected by using a different appropriate desaturase of the present invention. Examples of particularly useful compounds that can be derived from alkadiene precursors obtained by this method include Z7,Z11-16:Ac and Z7,E11-16:Ac, the two principal components of the pheromone of the major pest, $Pectinophora$ $gossypiella$, the pink boll worm.

Selection and combination of the unique desaturase of the present invention, the specific acyl-CoA reactant, the post-desaturation modifications to the pheromone precursor are governed, of course, by the structure of the pheromones desired. Since the pheromone biosynthetic pathways and products are known for many species of insects, acyl-CoA reactants, specific desaturase employed, and modifications to the products are straightforward. The components of pheromones of most of the major lepidopteran pests and many other species are recited in Tóth et al., "List of Sex Pheromones of Lepidoptera and Related Attractants," Montfavet, France:International Organization for Biological Control, West Palearctic Regional Section (1992), which is hereby incorporated by reference. For those insect species for which the structures of pheromone components are not known, preferred acyl-CoA reactants can be easily ascertained by standard analytical chemistry procedures well known to those skilled in the art, as described, for example in Bjostad et al., "Pheromone Biosynthesis in Lepidopterans: Desaturation and Chain Shortening," In: Pheromone Biochemistry, Prestwich, G. D. and G. J. Blomquist (eds.), New York:Academic Press, pp. 77–120 (1987), which is hereby incorporated by reference.

The desaturase of the present invention can be used in a number of ways to effect conversion of the acyl-CoA reactants. For example, the isolated desaturase can be used in an in vitro reactor by contacting the desaturase with the acyl-CoA reactant under conditions effective to convert the acyl-CoA reactant to the unsaturated fatty acyl-CoA product, analogous to the procedure used by Strittmatter et al., "Bacterial Synthesis of Active Rat Stearyl-CoA Desaturase Lacking the 26-residue Amino-terminal Amino Acid Sequence," $J.$ $Biol.$ $Chem.$, 263:2532–2555 (1988), which is hereby incorporated by reference. Generally, such reactions are effected by reconstituting a functional desaturase complex, such as one comprising the isolated desaturase, cytochrome b5, and cytochrome b5 reductase in an artificial lipid bilayer consisting of phosphatidylcholine, in suspension in a buffer, preferably 50 mM phosphate (pH 7.5 to 8.0, preferably 7.8), 1 mM β-mercaptoethanol or dithiothriotol, cofactors, such as NADPH or NADH (50 mM), and the acyl-CoA reactant. Following conversion, the unsaturated fatty acid product can be isolated and purified by standard methods, such as solvent extraction, distillation, chromatography, and the like. The desaturase can be provided, for example, by culturing a host cell of the present invention under conditions effective to express the membrane associated desaturase, as described above.

In a preferred embodiment, conversion of the saturated or unsaturated fatty acyl-CoA reactant to the unsaturated fatty acyl-CoA product is effected in a bioreactor by culturing a host cell, such as the yeast, $Saccharomyces$ $cerevisea$, under conditions effective for the cell to produce a functional recombinant desaturase. The expressed functional hybrid enzyme mediates formation of unsaturated acyl-CoA products having the position and stereospecificity of the double-bond determined by the supplied insect desaturase sequences. The unsaturated acyl-CoA products produced in this in vivo system can themselves be potential substrates for other enzymes occurring endogenously in the host cell and comprising its natural biochemical pathways, which mediate the formation of unique substituted and unsubstituted unsaturated hydrocarbon products having the position and stereospecificity of unsaturation specified by the supplied desaturase sequences.

One embodiment of the present invention consists of the acyl-CoA desaturase being expressed in cells of the yeast, $Saccharomyces$ $cereviseae$, which can be grown either in a fermentor or by other standard batch methods employing complete, liquid medium at 30° C., well known to those skilled in art, such as described in Kaiser et al., $Methods$ $in$ $Yeast$ $Genetics$, Cold Spring Harbor Laboratory Press (1994), which is hereby incorporated by reference.

The present invention also provides for a cassette cloning procedure by which an unsaturated fatty acyl-CoA product is produced. The method includes providing an olel desaturase-deficient strain of yeast host cell transformed with an expression system and culturing the host cell under conditions effective to produce the unsaturated fatty acyl-CoA product. The expression system comprises a DNA molecule encoding a catalytic domain of a membrane-associated desaturase expressed in the pheromone gland of an insect and a yeast OLE1 Δ9 desaturase promoter. The core region of the Δ9 desaturase promoter is replaced by the DNA molecule encoding the catalytic domain. The structure of the expression vector is detailed in U.S. Pat. No. 5,057,419 to Martin et al., Stukey et al., $J.$ $Biol.$ $Chem.$ 264:16537–16544 (1989), and Stukey et al., $J.$ $Biol.$ $Chem.$ 265:20144–20149 (1990), all of which are hereby incorporated by reference. Briefly, the OLE1 vector is modified by first cutting the vector at a naturally occurring Eco RI site at nucleotides 1362–1367. These 6 nucleotides comprise the two codons for glutamic acid (GAA) and phenylalanine (TTC) and are positioned immediately adjacent to the 3' PCR target sequence encoding the conserved amino acid sequence motif HNYHH (SEQ. ID. No. 12). This facilitates ligation of the 3' end of the PCR product in the homologous position and in proper frame with the yeast C-terminal amino acids. The 5' accepting site of the vector is generated by cutting with BstE II (GGTNACC) and digestion of the 5' overhang with Mung Bean nuclease or S1 nuclease. The 5' end of the PCR product (beginning with the sequence GTTAC) is then blunt end-ligated in frame with the yeast N-terminal amino acids as depicted in FIG. 1. Constructs made in this way contain the yeast OLE1 Δ9 desaturase promoter and coding region for the first 160 N-terminal amino acid residues and the last 221 C-terminal amino acid residues of the yeast desaturase, with the region coding for the 179 central amino acid residues replaced by homologous, in-frame, insect desaturase coding regions. Fusion constructs are used to transform the olel yeast strain, and the expressed gene product is isolated and optionally purified as described above.

The pheromones provided by the methods of the present invention can be used in a variety of ways. For example, the pheromones can be used to attract insects of a particular species to a trap, where they are either restrained or killed. Details regarding the use and construction of moth traps are disclosed in U.S. Pat. No. 4,147,771 to Struble et al., U.S. Pat. No. 5,236,715 to McDonough et al., U.S. Pat. No. 3,991,125 to Labovitz et al., U.S. Pat. No. 3,803,303 to McKibben et al., U.S. Pat. No. 3,980,771 to Meijer et al., U.S. Pat. No. 4,834,745 to Ogawa et al. and U.S. Pat. No. 4,600,146 to Ohno, which are hereby incorporated by reference.

The pheromones can be used to detect the location and boundaries of localized insect infestation and to monitor insect populations. Such a method can employ the above-described traps, placed at strategic locations within and near the suspected area of infestation. The quantity of insects trapped at each of these strategic locations would permit a mapping of the boundaries of insect infestation. Alternatively, the pheromone can be placed on a support and the number of insects approaching the support counted electronically, optically, mechanically, or otherwise, without trapping, restraining, killing, or otherwise incapacitating the insects. In this way, an estimate of the insect population density can be obtained. The area of localized infestation can then be treated with biocontrol agents or insecticides or both, thus permitting efficient and directed use of such biocontrol agents and insecticides. Further details regarding the use of insect attractants to detect and locate areas of insect infestation are disclosed in U.S. Pat. No. 5,236,715 to McDonough et al., and U.S. Pat. No. 3,980,771 to Meijer et al., which are hereby incorporated by reference.

The insect pheromones can also be used to disrupt mating of insects within a particular area. This method includes providing in the particular area a quantity of a pheromone above that emanating from insects, preferably a quantity sufficient to prevent pheromone communication. In this manner, potential mates are prevented from finding each other, thus disrupting the ability of the insects to mate. The pheromone can be sprayed or deposited in the particular area in a suitable carrier, such as vegetable oil, refined mineral oil, rubber, plastic, silica, diatomaceous earth, and cellulose powder. Alternatively, the attractant can be provided by evaporating the pheromone, its solution, or its emulsion from a number of places in the particular area. Further details regarding disruption of moth mating are disclosed in U.S. Pat. No. 3,980,771 to Meijer et al., which is hereby incorporated by reference.

The pheromones can also be blended with an insecticide. Because many insecticides repel insects, the combination of a pheromone and insecticide can have enhanced effectiveness over use of an insecticide alone. The insecticide/pheromone blend can be in the form of, for example, sprays, such as emulsifiable concentrates or wettable powders, aerosols, dusts, baits, granular formulations, and laminated slow release formulations. The pheromones, combined with the insecticide and used without a support, can be spread over the area of insect infestation, preferably as a mist or a dust in a suitable carrier, such as vegetable oils, refined mineral oils, rubbers, plastics, silica, diatomaceous earth, and cellulose powder.

Further details regarding the combination of pheromones and insecticides in sprays, on supports, or in traps are disclosed in, for example, U.S. Pat. No. 5,236,715 to McDonough et al., which is hereby incorporated by reference.

Suitable insecticides for use in the aforementioned traps and blends include, for example, organophosphates, such as diazinon, chlorpyrifos, propetamphos or acephate, carbamates, such as propoxur, pyrethroids, such as cypermethrin, sulfluramids, insect growth regulators, or mixtures thereof. S,S'-(2-dimethylaminotrimethylene) bis (thiocarbamate) ("Cartap"), ethyl 2-dimethoxythiophosphorylthio-2-phenylacetate ("Phenthoate"), available commercially under the name ELSAN™ (Rhodia Agro), 1- (2-chlorobenzoyl)-3-(4-trifluoromethoxyphenyl)urea ("Triflumuron"), available commercial under the name ALSYSTIN™ (Bayer), and abamectin, available commercially under the name VERMECTIN™ (Merck), are preferred. Further details respecting these and other suitable insecticides are disclosed in Worthing, ed., *The Pesticide Manual,* 9th Ed., British Crop Protection Council, which is hereby incorporated by reference.

The pheromones can also be used in combination with a biocontrol agent. A biocontrol agent is defined as any biological enemy (e.g., predator, pathogen, parasite) of the insect. Examples of biocontrol agents include pathogenic nematodes, fungi, yeast, bacteria, and viruses. In use, the attractant lures insects to the biocontrol agent/pheromone composition where the insects are infected with the biocontrol agent. The insects then return to the general insect population and disseminate the agent to the rest of the population. As a result, an entire infestation of insects can be reduced by luring and infecting a few members of the population with the appropriate pathogen.

The biocontrol agent/pheromone insect control composition can be in the form of, for example, a spray, such as emulsifiable concentrates or wettable powders, aerosols, dusts, baits, granular formulations, and laminated slow release formulations. The pheromones can be combined with the biocontrol agent, without a support, and spread over the area of insect infestation, preferably as a mist or as a dust in a suitable carrier, such as vegetable oils, refined mineral oils, rubbers plastics, silica, diatomaceous earth, and cellulose powder. Alternatively, the pheromone can be combined with the agent on a support. Biocontrol agent/pheromone insect control compositions on supports are advantageous, because they eliminate the need to spread biocontrol agents unnecessarily. Because the mechanism by which biocontrol agents operate requires return of the infected insect to the population, the support is preferably used without an insecticide or restraining member.

It is also envisioned that chemosterilants can be used in conjunction with the insect pheromones to attract and sterilize male insects. Methods for exposing insects with the chemosterilant/pheromone insect control compositions are analogous to those used for exposing insects with the biocontrol agent/pheromone compositions.

Further details regarding the preparation and use of combination of biocontrol agent/pheromone and chemosterilant/pheromone insect control compositions are disclosed, for example, in U.S. Pat. No. 5,236,715 to McDonough et al., which is hereby incorporated by reference.

The pheromones can also be used to attract insects to a particular location by providing at the particular location about 10 picograms to about 10 milligrams, preferably about 1 nanogram to about 1 microgram of the pheromone. Proximate to the particular location, insects attracted with the aforementioned method can be exposed to an agent which impairs their ability to mate, thereby controlling the insect population. Suitable insect control agents include, for example, insect restraining devices, insecticides, biocontrol agents, or chemosterilants, as described above. The method of attracting moths can also be used to draw insects away from sensitive locations to less sensitive locations, such as, for example, from a region where the insect damages a particular crop to a region where no such crop is cultivated.

The following examples are offered by way of illustration, not limitation, of the present invention.

EXAMPLES

Example 1

Desaturase Conservation.

Figure 2:
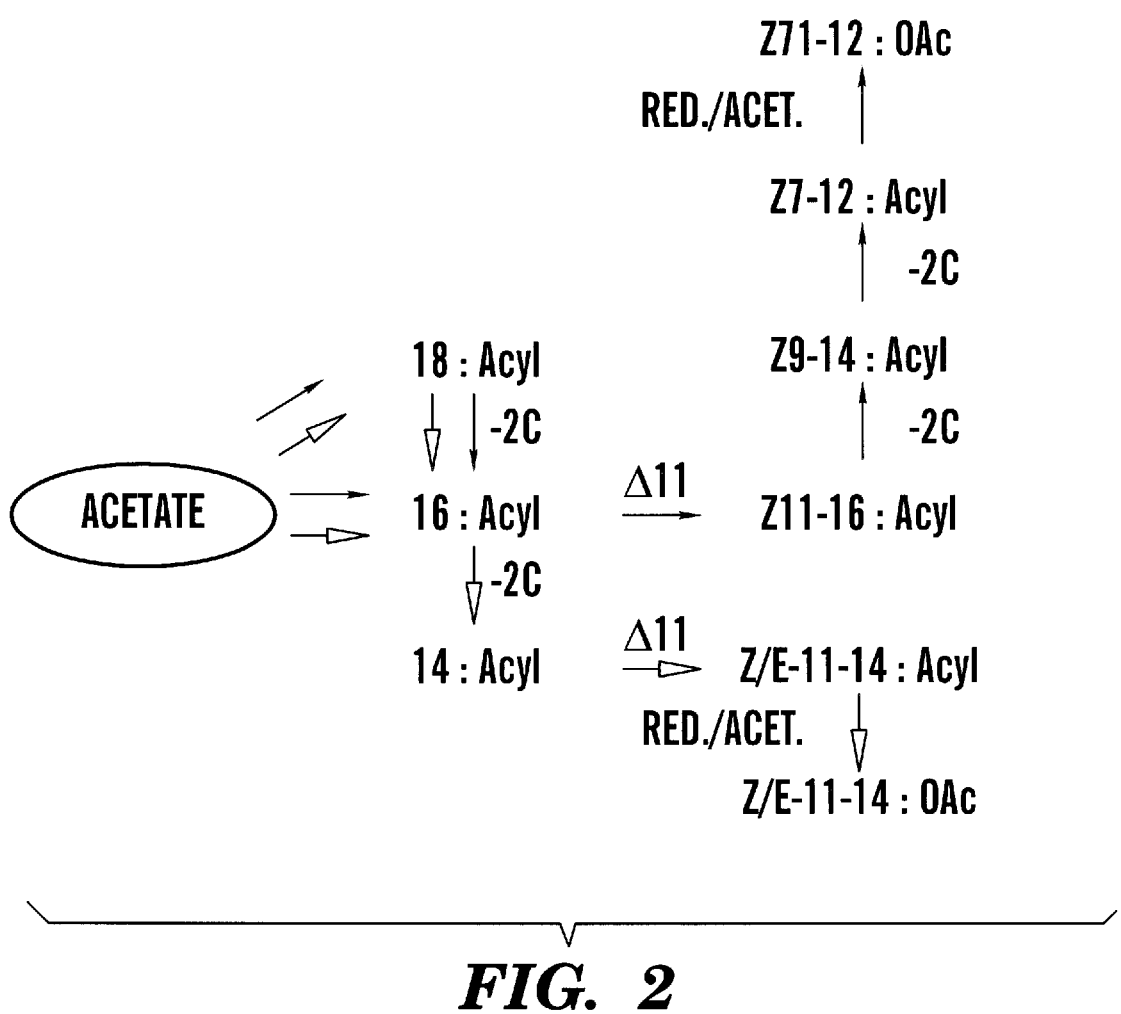
FIG. 2 is a diagram depicting biosynthetic routes for the major sex pheromone components in the cabbage looper and redbanded leafroller moths.

Several different Δ11 desaturases exist in lepidopteran species (Wolf et al., "Properties of the Δ11-desaturase enzyme used in cabbage looper moth sex pheromone biosynthesis," *Arch. Insect Biochem. Physiol.* 3:45–52 (1986); Wolf et al., "Reinvestigation confirms action of Δ11-desaturases in spruce budworm moth sex pheromone biosynthesis," *J. Chem. Ecol.* 13:1019–1027 (1987); Wolf et al., "Enzymes involved in the biosynthesis of sex pheromones in moths," in *Biocatalysis in Agricultural Biotechnology*, Whitaker et al., eds., American Chemical Society Symposium Series, pp. 323–331 (1989); Rodriguez et al., "Characterization of the delta-11-palmityl-CoA-desaturase from *Spodoptera littoralis* (Lepidoptera, Noctuidae)," *Insect Biochem. Molec. Biol.* 22:143–148 (1992), each of which is hereby incorporated by reference. Female cabbage looper moth pheromone glands produce only the Z isomer of 16- and 18-carbon monounsaturated acids, as well as a small amount of the Z isomer of the monounsaturated 14-carbon acid. The intermediate, Z11-16:Acyl, is chain shortened with subsequent reduction and acetylation to produce the major pheromone component, Z7-12:OAc as illustrated in FIG. 2. In contrast to the situation in the cabbage looper moths, the pheromone glands of redbanded leafroller moths produce both E and Z isomers of 14-carbon chain acids, but no unsaturated 16- or 18-carbon acids. The mixture of 14-carbon acids is reduced and acetylated to produce a specific 91:9 blend of Z/E11-14:OAc. Investigation of the spruce budworm and European corn borer moths, revealed that they produce a mixture of E and Z isomers of 14-carbon acids and pure Z11-16:COOH. The light brown apple moth Δ11 enzyme produces only pure E isomer with both 16- and 14-carbon chain acids (Foster et al., "Biosynthesis of a monoene and a conjugated diene sex pheromone component of the light brown apple moth by E11-desaturation," *Experientia* 46:269–273 (1990), which is hereby incorporated by reference). The evidence suggests that there exists a family of Δ11 desaturases with different isomeric and chain length specificities. Because evidence (Wolf et al., "Enzymes involved in the biosynthesis of sex pheromones in moths," in *Biocatalysis in Agricultural Biotechnology*, Whitaker et al., eds., American Chemical Society Symposium Series, pp. 323–331 (1989), which is hereby incorporated by reference) suggests the presence of only one Δ11 desaturase in the cabbage looper moth pheromone gland, this species is used to illustrate the method of the present invention. However, as indicated above the present invention is applicable to and contemplates isolation of desaturases found in moth pheromone glands producing multiple desaturases as well as other useful desaturases in other insect orders, such as flies or bees.

Figure 3:
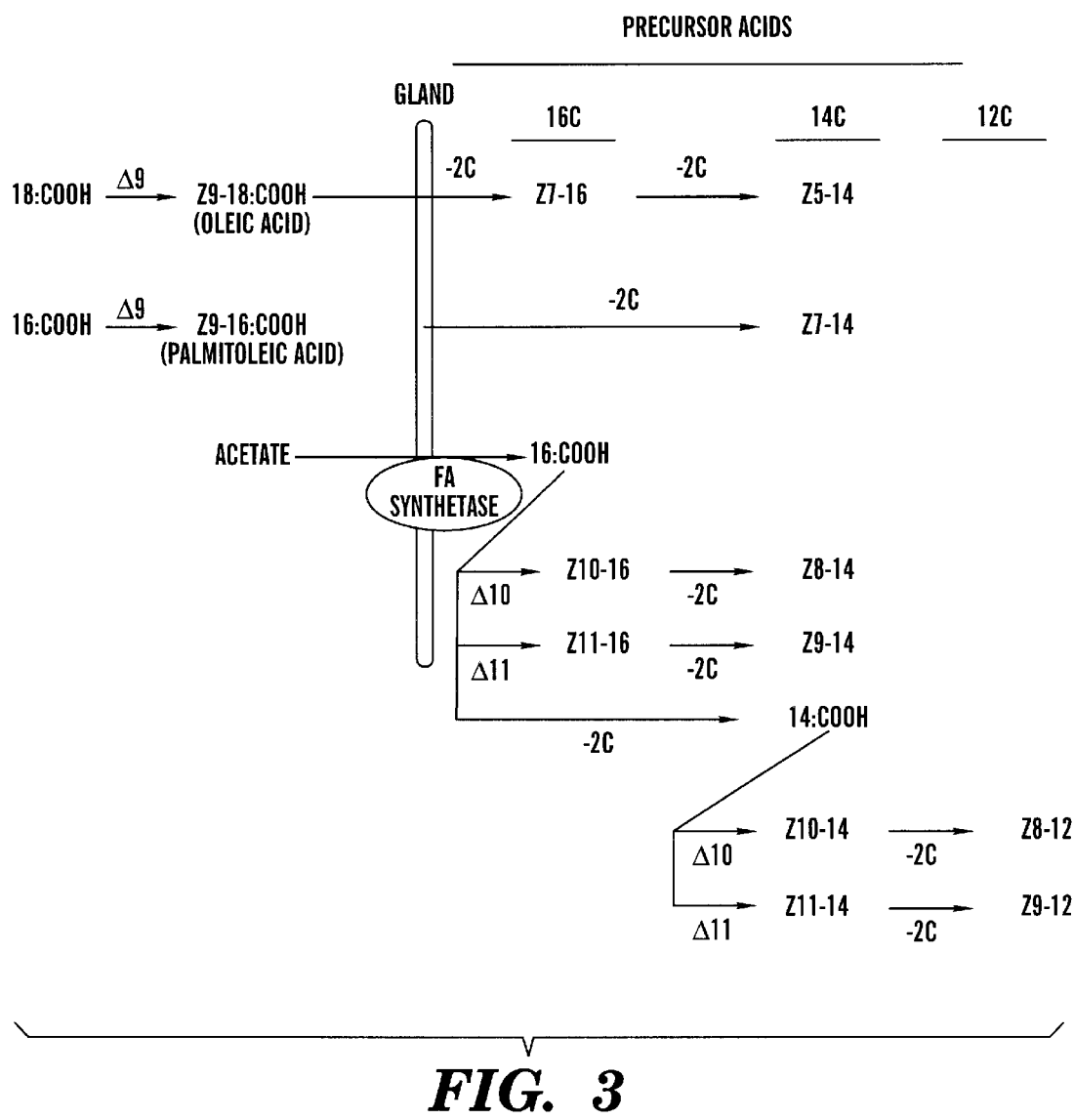
FIG. 3 is a diagram summarizing biosynthetic pathways in the Tortricidae for producing most of the known pheromone component precursors.

Desaturases with different positional specificities also have been found in moth sex pheromone glands. In addition to the family of Δ11 desaturases, Z10, E9, E14, and Z14 desaturation has been documented in moth pheromone biosynthesis (Foster et al., "Sex pheromone biosynthesis in the leafroller moth, *Planotortrix excessana* by Δ10 desaturation," *Arch. Insect Biochem. Physiol.* 8:1–9 (1988); Lofstedt et al., "Sex pheromone biosynthesis in the codling moth *Cydia pomonella* involves E9-desaturation," *J. Chem. Ecol.* 14:903–915 (1988); Roelofs et al., "Pheromone biosynthesis in the Lepidoptera," *J. Chem. Ecol.* 14:2019–2031 (1988); Zhao et al., "Sex pheromone biosynthesis in the Asian corn borer *Ostrinia furnacalis* (II): Biosynthesis of (E)- and (Z)-12-tetradecenyl acetate involves Δ14 desaturation," *Arch. Insect Biochem. Physiol.* 15:57–65 (1990), each of which is hereby incorporated by reference). In defining pheromone pathways employing different desaturase systems in the Tortricidae, several trends that could be key to the evolution of these pheromone systems have been noted. The most striking trend in these data is that species using pheromone components produced from extracellular oleic or palmitoleic acid (Δ9 desaturase) or from Δ10 desaturase pathways usually possess plesiomorphic characters, a term used by taxonomists to denote primitive anatomical features. A survey of 19 Tortricidae species from New Zealand conducted by Foster et al., "A comparison of morphological and sex pheromone differences in some New Zealand Tortricinae moths," *Biochem. Syst. Ecol.* 16:227–232 (1988), which is hereby incorporated by reference, showed that 9 of 19 species are distinct from the rest and are classified as primitive. All 9 species were found to use pheromone components that have biosynthetic pathways involving either Δ10- or Δ9-unsaturated precursors. These pathways are summarized in FIG. 3.

That Δ9- or Δ10-desaturated precursors represent an ancestral character for tortricids is further supported by Horak et al., "Pheromone components of some Australian tortricids in relation to their taxonomy," *J. Chem. Ecol.* 14:1163–1175 (1988), which is hereby incorporated by reference, which presents a survey of 30 tortricid species in Australia. In this study, over half the species used pheromone components derived by way of Δ11 desaturation, but none of the primitive members of the Tortricinae or Olethreutinae tribes used pheromone components involving Δ11 desaturation. Again, the species possessing ancestral characters used pheromone components with unsaturation in the 5, 7 or 9 position from Δ9 desaturation, or in the 8 or 10 position from ΔΔ10 desaturation. From this general trend of pheromones in the Tortricidae it is hypothesized that limited chain shortening in the microsomes evolved first to produce unique components from available oleic and palmitoleic acids. The ubiquitous Δ9 desaturase system could also have been involved in producing the precursor acid Z9-14:COOH, which is found in some primitive species in New Zealand and Australia. Mutation of the Z9 desaturase then could account for the occurrence of the unique Δ10 desaturase system found in the primitive leafroller species. Although one could argue strongly for many other evolutionary processes to explain the observed trends, it is nevertheless apparent that the unique acyl-CoA desaturases employed in the pheromone biosynthetic pathways of lepidoptera are derived from a common ancestral gene and have unusual, highly specialized functional properties consistent with their central role in the moth sexual communication system.

Example 2

Evaluation of the Temporal Maximum of Pheromone Production.

Since the amount of moth tissue containing pheromone biosynthetic desaturases is typically limiting, it is important to know when this enzyme is maximally present in the pheromone gland so that the most appropriate stage can be used. This is typically accomplished in accordance with Tang et al., "Development of functionally competent cabbage looper moth sea pheromone glands," Insect Biochem. 21:573–581 (1991), which is hereby incorporated by reference. Briefly, (1) titers of pheromone and intermediates of pharate adult and adult glands are examined, (2) gland culture technique is employed to determine when the pheromone biosynthetic enzymes become functionally present, (3) changes in the patterns of expressed proteins in in vivo gland culture and in vitro translated mRNAs for both non-competent and competent pheromone glands are characterized, (4) enzyme activity levels of non-competent and competent glands are compared, and (5) the correlation between the declining level of ecdysteroid and the onset of pheromone biosynthesis in pharate adults is determined.

In the cabbage looper moth, in contrast to adult pheromone glands, glands from pharate adults 2 days before eclosion were non-competent, had undetectable levels of pheromone and precursors, showed no Δ11 desaturase activity, and failed to incorporate radiolabeled acetate into pheromone in gland cultures. Glands had low levels of pheromone titer 1 day before adult eclosion, but by the time of eclosion were fully competent. Glands from 1-day old females exhibited the highest levels of pheromone biosynthetic activity using radiolabeled acetate. SDS-PAGE autoradiographic analysis of proteins synthesized in vivo (in gland culture) and in vitro (from stage specific mRNAs) showed similar profiles for both methods and revealed a number of proteins that were unique to the adult glands. In addition, pheromone production in cabbage looper was not controlled by Pheromone Biosysnthesis Activating Neuropeptide ("PBAN") as in other moth species, but competency was linked to changes in the ecdysteroid titer. On the basis of these results, glands obtained from newly eclosed (0–12 hr) adult females provide the most appropriate sources of mRNA for isolating a Δ11 desaturase cDNA clone.

Example 3

Isolation of mRNA.

A reliable mRNA purification procedure that could be used relatively easily with these small tissue sources was developed. Glands were dissected from either pupae or adult moths, and aliquots of an acid quanidinium isothiocyanate-phenol-chloroform extraction buffer (modified from Chomczynski et al., "Single-step method of RNA isolation by acid guanidinium thiocyanate-phenol-chloroform extraction," Anal. Biochem. 162:156–159 (1987), which is hereby incorporated by reference) containing 50–100 glands were frozen in liquid nitrogen and stored at −80° C. until useful quantities had been collected. This procedure produces consistent yields of about 200 μg of total RNA from 1,000 extirpated glands, which yields about 5 μg of intact poly-A+RNA and is further described in Tang et al., "Construction of a cDNA Library from Cabbage Looper Moth Sex Pheromone Glands," Molecular Insect Science, Hagedorn et al., eds., New York:Plenum, p. 368 (1990), which is hereby incorporated by reference. Poly-A+RNA prepared by this procedure was used as template in reverse transcription reactions to make cDNA. The latter was used as template in PCR reactions (described below) and to construct two separate cDNA libraries (one using oligo-dT and the other using random hexamers for first strand synthesis) in the λZAP cloning vector, each containing a minimum of 600,000 clones.

Example 4

Design of PCR Primers.

Primers were designed to amplify the specific cDNA sequence encoding the upstream conserved amino acid sequences His-Arg-Leu-Trp-Thr-His (SEQ. ID. No. 13) or His-Arg-Leu-Trp-Ser-His (SEQ. ID. No. 14) and the downstream conserved amino acid sequences His-Asn-Tyr-His-His-Tyr (SEQ. ID. No. 15), His-Asn-Tyr-His-His-Phe (SEQ. ID. No. 16), His-Asn-Phe-His-His-Tyr (SEQ. ID. No. 17), or His-Asn-Phe-His-His-Phe (SEQ. ID. No. 18), two regions of amino acid sequence identity between the published mammalian (SEQ. ID. No. 19) and yeast (SEQ. ID. No. 20) desaturase sequences illustrated in FIG. 4. The histidine residues in these conserved sequence motifs have recently been demonstrated to be essential for catalytic function (Shanklin et al, Biochemistry 33:12787–12794 (1994) ("Shanklin"), which is hereby incorporated by reference). The 5' (upstream) primer (5'Δ9d1 Primer) is complementary to a first strand cDNA sequence (antisense strand obtained by reverse transcription of a desaturase encoding mRNA). The 3' (downstream) primer (3'Δ9d2 Primer) is complementary to the sense cDNA strand obtained by specific priming and extension with the 5'Δ9d1 Primer.

In Δ9 desaturases of yeast and vertebrates, the length of the desaturase coding region delimited by these two primers is conserved (546 bp). Because of this conservation of length between the two targeted sequences, it was predicted that specific amplification products obtained from PCR reactions employing the above primers and cDNA templates made from pheromone glands would be approximately the same size as those resulting from amplification of Δ9 desaturase cDNAs of rat and yeast.

The 3'Δ9d2 and 5'Δ9d1 primers have sequences corresponding to SEQ. ID. No. 10 and SEQ. ID. No. 11, respectively, as follows:

SEQ. ID. No. 10:  5' CCC CAY CRN CTS TGG WCN CAY 3'

SEQ. ID. No. 11:  5' CCC <u>TCTAGA</u> RTG RTG RWA RTT RTG RWA 3'
                                 XbaI

The first three nucleotides of both primers are nonspecific "C clamps". To facilitate cloning of the amplification product, an XbaI site (TCTAGA) was incorporated in the 3'Δ9d2 Primer. In the case of the 5'Δ9d1 Primer, substitutions in the fifth codon (second triplet from the right) specify two amino acids (Ser and Thr). The number of sequence permutations for the 3'Δ9d2 and 5'Δ9d1 primers is 512 and 128, respectively. In the 3'Δ9d2 Primer, substitutions in the first codon (far right triplet) and third codon (third triplet from the right) specify two amino acids (Phe and Tyr).

Example 5

Isolation of Desaturase-encoding cDNA.

Δ11 desaturase cDNA was isolated employing the PCR-based homology probing strategy described in Gould et al., "Use of the DNA polymerase chain reaction for homology probing: Isolation of partial cDNA or genomic clones encoding the iron-sulfur protein of succinate dehydrogenase from several species," *Proc. Natl. Acad. Sci. USA* 86:1934–1938 (1989); Kamb et al., "Identification of genes from pattern formation, tyrosine kinase, and potassium channel families by DNA amplification," *Proc. Natl. Acad. Sci. USA* 86:4372–4376 (1989); Doyle et al., "PCR-based phylogenetic walking: isolation and sodium channel gene sequences from insects and mites by DNA amplification," *Insect Biochem.* 21:689–696 (1991); Knipple et al., "PCR-generated conspecific sodium channel gene probe for the house fly." *Arch. Insect Biochem. Physiol.* 16:45–53 (1991); Knipple et al., "Isolation of insect genes coding for voltage-sensitive sodium channels and ligand-gated chloride channels by PCR-based homology probing," in Neurotox '91, Molecular Basis of Drug and Pesticide Action, Duce, ed., Essex, U.K.: Elsevier Science Publishers Ltd., pp. 271–283 (1992); Henderson et al., "Characterization of a putative γ-aminobutyric acid (GABA) receptor β subunit gene from *Drosophila melanogaster*," *Biochem. Biophysic. Res. Comm.* 193:474–482 (1993); and Henderson et al., "PCR-based homology probing reveals a family of GABA receptor-like genes in *Drosophila melanogaster*," *Insect Biochem. Molec. Biol,.* 24:363–371 (1994), each of which is hereby incorporated by reference. To amplify putative desaturase-encoding gene sequences, primers described in Example 4 were used in PCR reactions containing cabbage looper moth pheromone gland cDNA. A 555 bp amplification product was isolated using primer set 1. The 555 bp length is the size predicted on the basis of the yeast and vertebrate sequences, taking into account the additional basepairs deriving from the C clamps incorporated into both primers and the XbaI restriction site incorporated into the 3'Δ9d2 Primer.

The 555 bp cDNA fragment was subsequently subcloned and its nucleotide sequence determined. The amplification product was digested with XbaI to generate a single 5' protruding end (at the site built into the 3'Δ9d2 Primer) and subsequently ligated into XbaI- and SmaI-digested pBluescript SK+. Following transformation of *E. coli* with the ligation mixture, insert-containing clones were isolated and sequenced according to the methods of Sanger et al., "DNA sequencing with chain-terminating inhibitors," *Proc. Natl. Acad. Sci. USA* 74:5463–5467 (1977), which is hereby incorporated by reference, using standard M13 forward and reverse sequencing primers and an Applied Biosystems model 373 automated DNA sequencer. The nucleotide sequence, SEQ. ID. No. 9, of the PCR product, amplified from *T. ni* pheromone glands using 5'Δ9d1 and 3'Δ9d2 Primers, and the inferred amino acid sequence, SEQ. ID. No. 5, are presented in FIG. 5 and FIG. 6, respectively. The sequence of the PCR product showed significant homology to the rat Δ9 desaturase with 102 identical amino acids corresponding to 56% sequence identity and an overall sequence similarity (taking into account conservative amino acid substitutions as well as identical amino acids) of 74%.

Example 6

Isolation of Full-length Δ11 desaturase cDNAs.

The above PCR product was labeled and used as a hybridization probe to screen pheromone gland cDNA libraries using standard procedures. Several positive clones were isolated and the sizes of the cDNA inserts they contained were determined. Clones with inserts greater than or equal to one kb in length were sequenced. Three of the first six sequences were found to have full length coding sequences as inferred from the existence of multiple stop codons at the 5' end in all three reading frames upstream from the first ATG initiating the largest open reading frame (1047 nucleotides; nt 82–1129 in FIG. 7). The full-length coding sequence, SEQ. ID. No. 8, and inferred amino acid sequence, SEQ. ID. No. 4, are presented in FIG. 7 and FIG. 8, respectively. The protein encoded by the ORF is 349 amino acids in length, estimated pI 8.945 and $M_r$ of 40,280 Da. Underlined sequences are the conserved target sequences used for the PCR. Sequence variants found in 3 independent clones at nt 46 and 64 in the 5' noncoding leader and at nt 97, 103, and 106 in the ORF resulted in no amino acid changes. One of the cDNA clones isolated had an A replaced by C at nucleotide position 208, indicated by an asterisk in FIG. 7, which produced an amino acid substitution of proline for threonine, at the position marked with an asterisk in FIG. 8.

The homology relationship of the full-length amino acid sequence, presented in FIG. 8, to yeast and vertebrate Δ9 desaturase sequences is illustrated by the computer-optimized alignment of all three sequences in FIG. 9. Numbering begins at the first Met residue of the yeast sequence. Overlined regions are the conserved histidine-containing motifs to which the degenerate target primers were designed. Hydrophobicity plots of the three amino acid sequences are shown in FIG. 10.

As illustrated in FIG. 9, the full length cDNA clone encodes a protein with 43.5% amino acid identity (60.5% taking into account conservative substitutions) to a rat Δ9 desaturase. The abundance of the encoding mRNA in the pheromone gland was extremely high, representing >2% of clones in the cDNA libraries. The predicted protein was also about the same size as the products synthesized in large quantities in both cultured glands form early adult stage and the products obtained by in vitro translation of pheromone gland mRNA from the same stage. In contrast, no product in this size range was detected in the corresponding products of pre-eclosion stage glands (Tang et al., "Development of functionally competent cabbage looper moth sex pheromone glands," *Insect Biochem.* 21:573–581 (1991), which is hereby incorporated by reference). These findings are consistent with this clone encoding the pheromone gland-specific Δ11 desaturase.

Example 7

Prokaryotic Expression.

To analyze the functional properties of the protein encoded by the cabbage looper cDNA, an appropriate construct to express the cDNA in *E. coli* was developed. The rat Δ9 desaturase cDNA clone pDS 3–358 (produced as described in Strittmatter et al., "Bacterial synthesis of active rat stearyl-CoA desaturase lacking the 26-residue amino-terminal amino acid sequence," *J. Biol, Chem.* 263:2532–2555 (1988), which is hereby incorporated by reference, and provided by Phillip Strittmatter), consisting of the rat Δ9 desaturase cDNA (encoding amino acid residues 3 to 358) inserted (via BamH1 restriction site at the 5' end and a Sac1 restriction site at the 3' end) into plasmid pUC8 in frame with the first 6 codons of the β-galactosidase gene was employed. The expressed fusion protein is thus under the (inducible) control of the lac promoter.

A plasmid construct was designed to express the T. ni Δ11 desaturase in E. coli in a manner that was strictly comparable to that used to express the rat Δ9 desaturase described above. This construct was made essentially by replacement of the coding region of the rat cDNA with the coding region of the T. ni cDNA. First, PCR primers were synthesized to match the 5' and 3' regions of the open reading frame of the putative Δ11; desaturase cDNA, and suitable restriction sites were incorporated at their 5' ends to facilitate subcloning. PCR primers were designed to match the first 6 amino acids of the T. ni desaturase (including an ATG start codon and a BamH1 restriction site) and the C terminal 6 amino acids (including a stop codon and a Sac1 restriction site). An extra "A" residue was also included between the desaturase start codon (ATG) and the BamH1 site (a "C") in order to place the T. ni desaturase ORF in the same reading frame as the 6 N-terminal codons of the β-galactosidase gene. These primers have sequences corresponding to SEQ. ID. No. 21 and SEQ. ID. No. 22, as follows:

5' Primer         GGGGGATCC A ATG GCT GTG ATG GCT CAA
(SEQ. ID. No. 21)     BamH1

3' Primer         GGGGAGCTC TCA TTC CTT TTT AGC ATA AAA
(SEQ. ID. No. 22)     Sac1

PCR was performed using these primers and the full length cDNA clone having the entire coding region of the Δ11 desaturase (FIG. 7) as a template. The amplification product was thus comprised of the entire coding region from start to stop codon bounded by a BamH1 site (and an additional "A" nucleotide) at the 5' end and a Sac1 site at the 3' end.

pDS 3-358 was digested with restriction enzymes (BamH1 and Sac1) to remove the rat Δ9 desaturase-encoding insert and the T. ni Δ11 insert was ligated in its place to give the recombinant plasmid pDS Δ11. The correct structure of the resulting plasmid (pDsat1) was verified by DNA sequencing.

The pDS3-358 plasmid-containing cells were used to express protein and served as functional assay controls for our analysis of the T. ni desaturase described below in Example 8. For expression E. coli XL1 Blue cells transformed with either pDsat1 or pDs3-358 were grown to a stationary phase in enriched medium containing iron (in the form of $FeCl_3$), which is a cofactor of the desaturase. Repression of the lac promotor achieved by the presence of glucose in the medium. Cells were then pelleted by centrifugation, washed to remove the glucose, and resuspended in a medium containing isopropylthiogalactoside to induce synthesis of the recombinant desaturases.

Example 8

Functional Assay of cDNA Clone.

Figure 11:
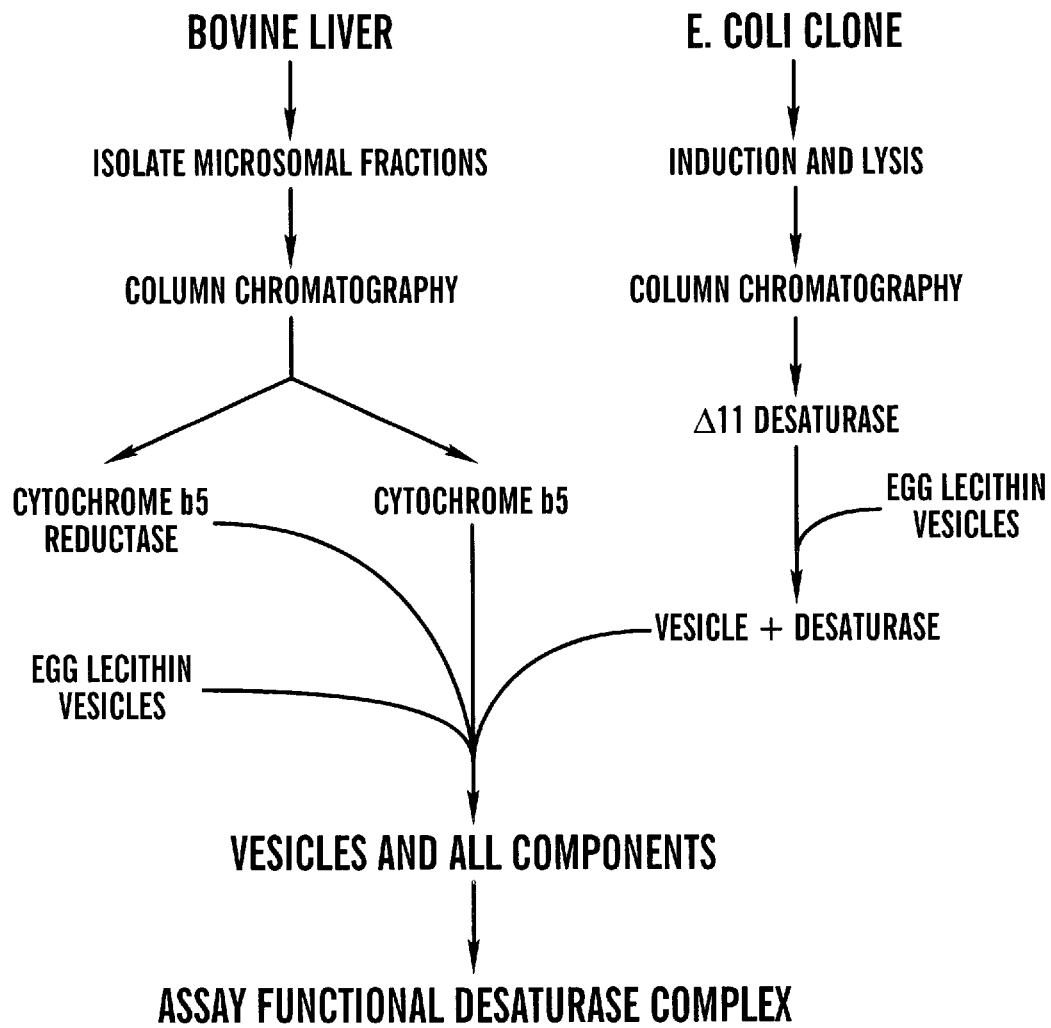
FIG. 11 is a flow diagram summarizing an assay for determining the functional identity of a *T. ni* desaturase clone, as detailed in Example 8.

To determine if the components of the desaturase functional complex could be reassembled to give an active preparation, the terminal stearoyl-CoA protein from rat was isolated from an E. coli strain in which the full length cDNA clone had been incorporated and expressed as described in Example 7. The method, analogous to that used by Strittmatter et al., "Bacterial synthesis of active rat stearyl-CoA desaturase lacking the 26-residue amino-terminal amino acid sequence," J. Biol. Chem. 263:2532–2535(1988), which is hereby incorporated by reference, is summarized in FIG. 11. The three components were pre-incubated with sonicated phospholipid and assayed for desaturase activity. The assay was performed by adding $[^{14}C]$-labeled palmitoyl-CoA, incubating for an hour, extracting the lipids, subjecting them to acid methanolysis, and performing TLC on the products using plates containing silver ions, which separate the saturated starting material from the desaturated product (Wolf et al., "Properties of the All-desaturase enzyme used in cabbage looper moth sex pheromone biosynthesis," Arch. Insect Biochem. Physiol. 3:45–52 (1986), which is hereby incorporated by reference). Monounsaturated $[^{14}C]$-palmityl CoA was observed, indicating the presence of desaturase activity and the reconstitution of a functional complex.

Figure 12:
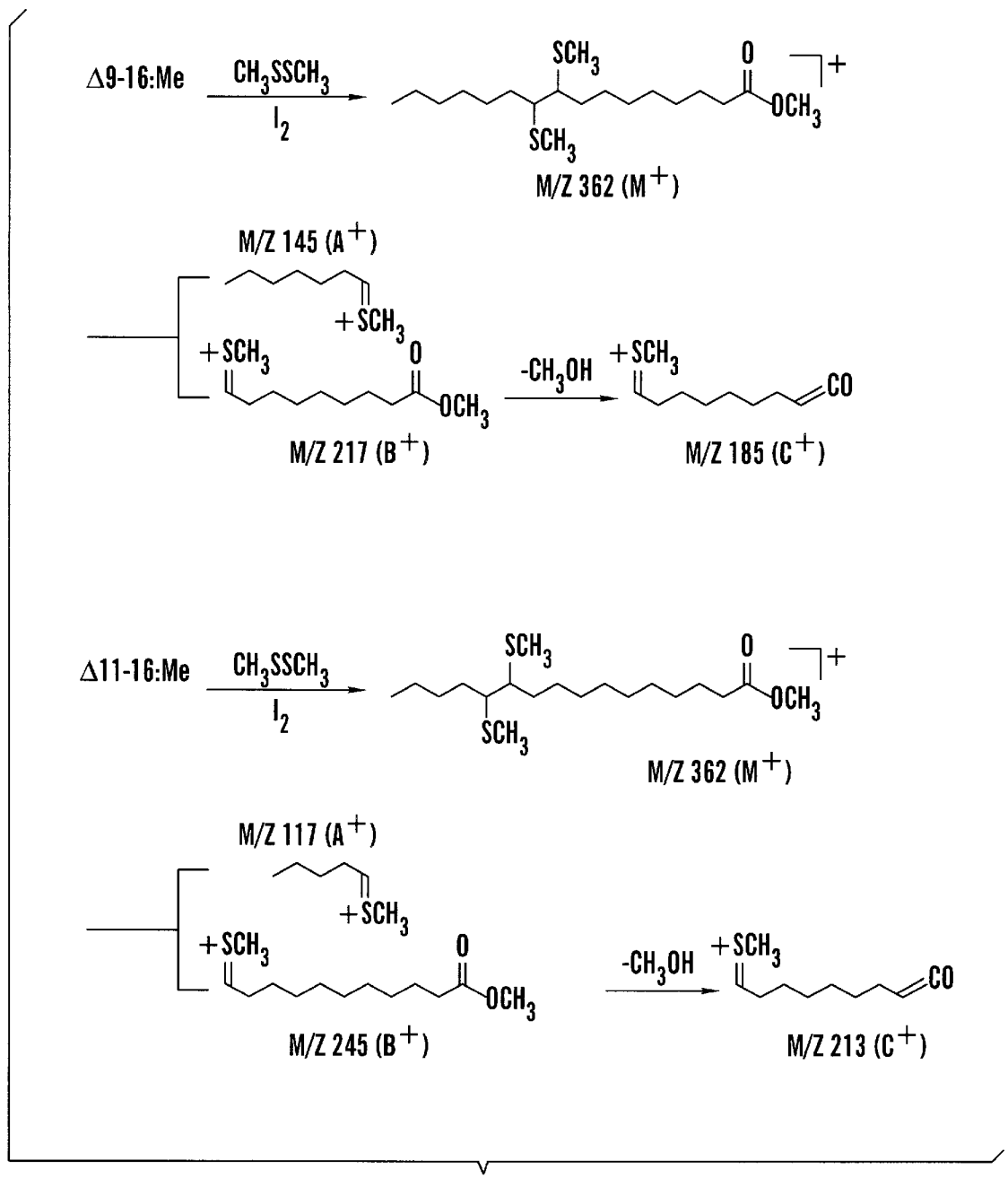
FIG. 12 shows the degradation pathways of dimethyl disulfide adducts of methyl Δ9 hexadecanoate and methyl Δ11 hexadecanoate, as described in Example 8.

To discriminate between the product of Δ9 desaturation and that of Δ11 desaturation, dimethyl disulfide ("DMDS") derivatives of the reaction products of deuterium-labeled palmitoyl-CoA ($[16,16,16-^2H_3]$hexadecanoyl CoA) were prepared using the method described in Buser et al., "Determination of double bond position in mono-unsaturated acetates by mass spectrometry of dimethyl disulfide adducts," Anal. Chem. 55:818–822 (1983), which is hereby incorporated by reference. The Z9- and Z11-16:Acids were clearly resolved by capillary GLC (carbowax 20M), and the structures confirmed by distinct mass spectra exhibiting two large methyl sulfide fragments for the Z9 isomer at m/z 145 and 217, compared to two large fragments for the Z11 isomer at m/z 117 and 245. Degradation pathways of DMDS adducts of Δ9 and Δ11 hexadecenoate are provided in FIG. 12. The omega-d3 resides in the hydrocarbon end fragment and, thus, product formation is determined by assessing the M+3 increase in the 145 and 117 fragments, respectively, when using labeled precursor. The DMDS products obtained from reactions containing the expressed cabbage looper moth protein demonstrated the presence of the Z11-16:Acid, indicating that the reconstituted desaturase activity of the cabbage looper moth desaturase mediated All desaturation.

Example 9

In vivo Expression in Saccharomyces cereviseae.

Previous work (Stukey et al., J. Biol. Chem. 264:16537–16544 (1989) ("Stukey 1989"), which is hereby incorporated by reference) has demonstrated the feasibility of expressing vertebrate Δ9 desaturases in a yeast mutant ole1 unable to express its own Δ9 desaturase. The subsequent complementation of such a yeast Δ9 deficient mutant is used as a convenient assay of desaturase function, and as a means to produce greater quantities of monounsaturated intermediates for the synthesis of insect pheromones. The wildtype yeast Δ9 desaturase gene (OLE 4.8), present in the yeast shuttle vector YEp352, was prepared as described in Stukey 1989, which is hereby incorporated by reference. Digestion of this plasmid with Sal1 deletes 3.7 kb of the 4.8 kb OLE1 insert, and produces a linearized plasmid (pOLE4.8-Sal1$^\Delta$) having the yeast OLE1 promoter consisting of 1.1 kb of DNA sequence upstream from the translation start site and having the first 78 nucleotides of the OLE1 ORF encoding the first (N-terminal) 27 amino acids of the OLE1 protein. As detailed in Stukey et al., J. Biol. Chem. 265:20144–20149 (1990) ("Stukey 1990"), which is hereby incorporated by reference, a region of the ORF of the rat Δ9 desaturase cDNA was removed from pDS 3-358 using BamH1 and Sac1 digests and was then ligated in the correct reading frame of the pOLE4.8-Sal1$^\Delta$ so that a fusion protein was encoded having residue number 3, alanine, of the rat desaturase following residue number 27, aspartic acid, of the yeast desaturase.

Similarly, the *T. ni* Δ11 desaturase ORF (isolated from pDSΔ11) was placed in frame relative to the first 27 amino acids of OLE1 encoded on pOLE4.8-Sal1^A.

This construct was then introduced into a yeast Δ9 desaturase-deficient mutant (yeast strain L840 C, prepared as described in Stukey 1990, which is hereby incorporated by reference) and tested for complementation of the mutant's unsaturated fatty acid requirement by the *T. ni* Δ11 desaturase.

Based on these results, a yeast cassette vector that permits insertion of PCR fragments (obtained using the degenerate PCR Primer Set 1 as described in Example 5) in place of the homologous sequences in the central core domain of the yeast Δ9 desaturase ORF is constructed. The region having the highest overall homology and including one strongly hydrophobic conserved domain is targeted for exchange. Bearing in mind the limited homology encountered as one proceeds toward the N-terminal and C-terminal ends from this central core region and the apparent lack of functional importance of the N-terminal end, it is anticipated that the catalytic domains of diverse desaturases will be contained in the central core or "cassette" region. Furthermore, published studies (Fox et al., "Resonance Raman evidence for an Fe-O-Fe center in stearoyl-ACP desaturase. Primary sequence identity with other diironoxo proteins." *Biochem.* 33:12776–12786 (1994), Avelangemacherel et al., "Site-directed mutagenesis of histidine residues in the delta-12 acyl-lipid desaturase of *Synechocystis*," *FEBS Letters* 361:111–114 (1995), and Shanklin, each of which is hereby incorporated by reference) have demonstrated that the highly conserved histine residues (underlined sequences in FIG. 4) are involved in iron binding and are, therefore, critical in the desaturation event. In view of these studies, the region targeted for exchange preferably contains these highly conserved histidine residues.

Figure 13:
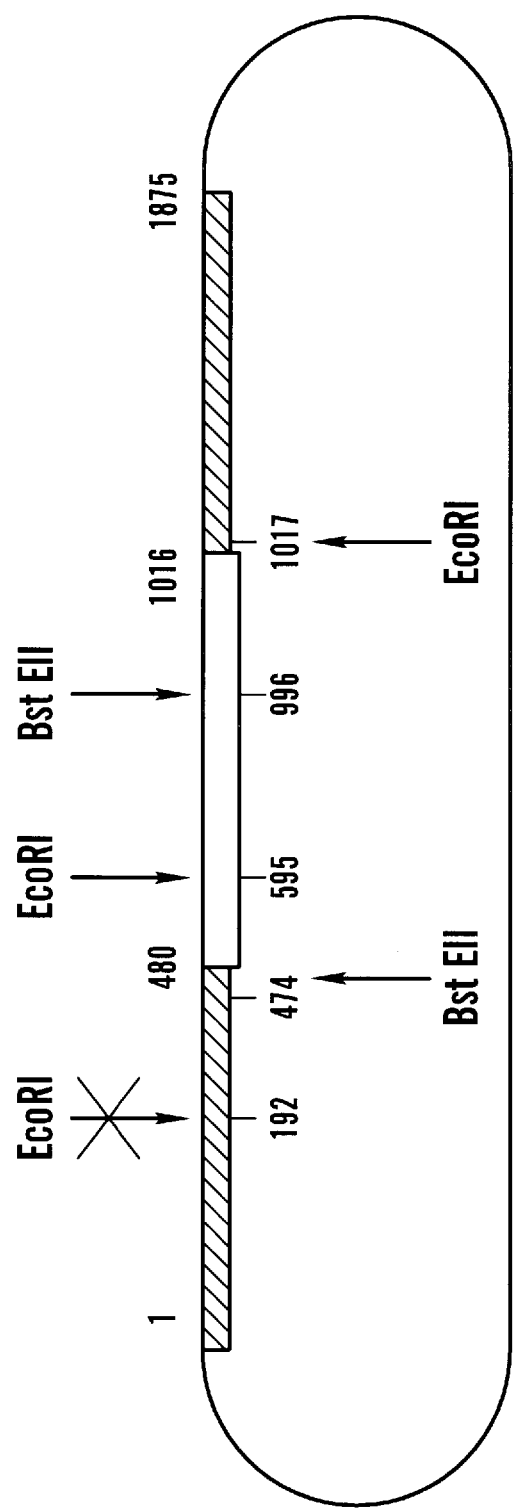
FIG. 13 shows a method to construct the yeast cassette vector for desaturase expression proposed in Example 9.

The cassette vector (depicted in FIG. 13) for desaturase expression is prepared by cutting the yeast OLE1 ORF (contained in yeast plasmid vector YEP352) with EcoRI (GAATTC) and BstEII (GGTNACC) after first mutating the EcoRI site at nt 192. First, the sequence GAATTC (encoding Glu, Phe) is changed to GAATTT (also encoding Glu, Phe) using in vitro mutagenesis with an appropriate oligonucleotide. The changed sequence is then digested with Bst EII to generate a 5' protruding end of sequence CAATG and 2 fragments, one of 522bp and the other of 1353 bp+vector sequence. The overhangs are then removed by digestion with Mung Bean Nuclease to produce blunt ends.

Digestion with EcoRI results in a linearized fragment comprising 1332 bp from OLE1 and vector sequences, which is a cassette-accepting vector with a 5' blunt end and a 3' EcoRI sticky end.

"Cassettes" that can be inserted into the above vector are PCR fragments derived from insect desaturase encoding cDNA sequences. The 5' PCR oligonucleotides used to generate a cassette start with GTTAC followed by any of the nucleotide sequences encoding the amino acid sequences corresponding to SEQ. ID. No. 13 or SEQ. ID.

No. 14. The 3' PCR oligonucleotides start with a C clamp and the EcoRI recognition sequence (CCCGAATTC) followed by any of the nucleotide sequences whose complementary strands encode the amino acid sequences corresponding to SEQ. ID. No. 15, SEQ. ID. No. 16, SEQ. ID. No. 17, or SEQ. ID. No. 18. Prior to its ligation to the vector, the PCR fragment is first digested with EcoRI to generate an EcoRI sticky end that can anneal to the EcoRI sticky end of the cassette accepting vector. The 5' end of the PCR product (beginning with the sequence GTTAC) is blunt end-ligated in frame with sequences encoding the yeast N-terminal amino acids as depicted in FIG. 6. Constructs made in this way will contain the yeast OLE1 Δ9 desaturase promoter and coding region for the first 160 N-terminal amino acid residues and the last 221 C-terminal amino acid residues, with the region coding for the 179 central amino acid residues being replaced by homologous, in-frame, insect desaturase coding regions. Such fusion constructs are then used to transform the olel yeast strain and the expressed gene products assayed by complementation of the olel strain's fatty acid requirement, and by the procedure described above for the in vitro assays.

Although the invention has been described in detail for the purpose of illustration, it is understood that such detail is solely for that purpose, and variations can be made therein by those skilled in the art without departing from the spirit and scope of the invention which is defined by the following claims.

---

What is claimed:

1. An isolated acyl-CoA desaturase corresponding to a membrane-associated desaturase expressed in the pheromone gland of an insect, wherein said desaturase is a *Trichoplusia ni* Δ11 desaturase.

2. An isolated acyl-CoA desaturase according to claim 1 having a molecular weight of about 40 kDa as calculated from amino acid sequences.

3. An isolated acyl-CoA desaturase according to claim 1 having a calculated isoelectric point from about 8.9 to about 9.0.

4. An isolated acyl-CoA desaturase according to claim 1, wherein said desaturase is recombinant.

5. An isolated acyl-CoA desaturase, wherein said desaturase has an amino acid sequence corresponding to SEQ. ID. No. 4.

6. An isolated acyl-CoA desaturase, wherein said desaturase comprises an amino acid sequence corresponding to SEQ. ID. No. 5.

* * * * *